US011230558B2

(12) United States Patent
Rinderspacher et al.

(10) Patent No.: US 11,230,558 B2
(45) Date of Patent: Jan. 25, 2022

(54) ACTIVATORS OF AUTOPHAGIC FLUX AND PHOSPHOLIPASE D AND CLEARANCE OF PROTEIN AGGREGATES INCLUDING TAU AND TREATMENT OF PROTEINOPATHIES

(71) Applicants: THE TRUSTEES OF COLUMBIA UNIVERSITY IN THE CITY OF NEW YORK, New York, NY (US); NY STATE PSYCHIATRIC INSTITUTE, New York, NY (US)

(72) Inventors: Kirsten Alison Rinderspacher, Mount Vernon, NY (US); Wai Yu, New York, NY (US); Karen Duff, New York, NY (US); Donald Landry, New York, NY (US); Shi-Xian Deng, White Plains, NY (US)

(73) Assignees: The Trustees of Columbia University in the City of New York, New York, NY (US); NY State Psychiatric Institute, New York, NY (US)

( * ) Notice: Subject to any disclaimer, the term of this patent is extended or adjusted under 35 U.S.C. 154(b) by 0 days.

(21) Appl. No.: 16/027,951

(22) Filed: Jul. 5, 2018

(65) Prior Publication Data
US 2018/0319818 A1 Nov. 8, 2018

Related U.S. Application Data

(60) Division of application No. 15/480,220, filed on Apr. 5, 2017, now Pat. No. 10,487,091, which is a continuation-in-part of application No. PCT/US2016/055561, filed on Oct. 5, 2016.

(60) Provisional application No. 62/237,342, filed on Oct. 5, 2015.

(51) Int. Cl.
C07D 513/04 (2006.01)
C07D 403/12 (2006.01)
C07D 405/12 (2006.01)
C07D 239/86 (2006.01)
C07D 239/93 (2006.01)
C07D 239/94 (2006.01)
C07D 471/04 (2006.01)
C07D 491/04 (2006.01)
C07D 495/04 (2006.01)
A61K 31/517 (2006.01)
C07D 217/22 (2006.01)
C07D 239/88 (2006.01)
C07D 401/12 (2006.01)
C07D 491/048 (2006.01)
A61P 25/28 (2006.01)

(52) U.S. Cl.
CPC .......... C07D 513/04 (2013.01); A61K 31/517 (2013.01); A61P 25/28 (2018.01); C07D 217/22 (2013.01); C07D 239/86 (2013.01); C07D 239/88 (2013.01); C07D 239/93 (2013.01); C07D 239/94 (2013.01); C07D 401/12 (2013.01); C07D 403/12 (2013.01); C07D 405/12 (2013.01); C07D 471/04 (2013.01); C07D 491/04 (2013.01); C07D 491/048 (2013.01); C07D 495/04 (2013.01)

(58) Field of Classification Search
CPC .................................................... C07D 513/04
See application file for complete search history.

(56) References Cited

U.S. PATENT DOCUMENTS

| | | |
|---|---|---|
| 3,266,990 A | 8/1966 | Lutz et al. |
| 3,272,824 A | 9/1966 | Ebetino et al. |
| 3,936,461 A | 2/1976 | Mortlock et al. |
| 4,114,939 A | 9/1978 | Burt |
| 5,145,843 A | 9/1992 | Arnold et al. |
| 5,650,415 A | 7/1997 | Tang et al. |
| 5,693,652 A | 12/1997 | Takase et al. |
| 6,002,008 A | 12/1999 | Wissner et al. |
| 6,103,728 A | 8/2000 | Tang et al. |
| 6,143,764 A | 11/2000 | Kubo et al. |
| 6,184,225 B1 | 2/2001 | Thomas et al. |
| 6,251,912 B1 | 6/2001 | Wissner et al. |
| 6,265,410 B1 | 7/2001 | Bridges et al. |
| 6,297,258 B1 | 10/2001 | Wissner et al. |
| 6,391,874 B1 | 5/2002 | Cockerill et al. |
| 6,596,727 B1 | 7/2003 | Schaper et al. |
| 6,630,489 B1 | 10/2003 | Crawley |
| 6,919,338 B2 | 7/2005 | Mortlock et al. |
| 6,995,174 B2 | 2/2006 | Wang et al. |
| 7,081,461 B1 | 7/2006 | Mortlock et al. |

(Continued)

FOREIGN PATENT DOCUMENTS

| | | |
|---|---|---|
| CA | 2417955 A1 | 1/2003 |
| CN | 1083811 A | 3/1994 |

(Continued)

OTHER PUBLICATIONS

STN RN 1401991-136-6 (2012).*
STN RN 929503-36-6 (2007).*
STN RN 929370-68-3 (2007).*
Chemspider, 6-Fluoro-4-(tetrahydro-2H-pyran-4-ylsulfanyl)quinazoline, Royal Society of Chemistry, 2015, Retreived from the Internet <URL http://www.chemspider.com/Chemical-Structure_30132867.html?rid=9a2b8938-1827-42ad>.

(Continued)

Primary Examiner — Paul V Ward
(74) Attorney, Agent, or Firm — Venable LLP

(57) ABSTRACT

The present application discloses compounds which are activators of autophagic flux and pharmaceutical compositions comprising said activators. It further discloses use of said compounds and pharmaceutical compositions in the treatment of neurodegenerative diseases, particularly proteinopathies and tauopathies such as Alzheimer's disease. It further discloses methods of enhancing autophagic flux.

23 Claims, 5 Drawing Sheets

(56) References Cited

U.S. PATENT DOCUMENTS

| | | |
|---|---|---|
| 7,135,466 B2 | 11/2006 | Sakai et al. |
| 7,141,577 B2 | 11/2006 | Ple |
| 7,173,135 B2 | 2/2007 | Hennequin et al. |
| 7,173,136 B2 | 2/2007 | Hennequin et al. |
| 7,211,587 B2 | 5/2007 | Kubo et al. |
| 7,262,201 B1 | 8/2007 | Hennequin et al. |
| 7,268,230 B2 | 9/2007 | Hennequin |
| 7,402,583 B2 | 7/2008 | Boyle et al. |
| 7,425,564 B2 | 9/2008 | Fujiwara et al. |
| 7,432,377 B2 | 10/2008 | Chew et al. |
| 7,462,623 B2 | 12/2008 | Ple |
| 7,479,473 B2 | 1/2009 | Queen |
| 7,495,104 B2 | 2/2009 | Miwa et al. |
| 7,504,408 B2 | 3/2009 | Hennequin et al. |
| 7,560,558 B2 | 7/2009 | Shimizu et al. |
| 7,598,258 B2 | 10/2009 | Kubo et al. |
| 7,601,716 B2 | 10/2009 | Dorsey et al. |
| 7,763,731 B2 | 7/2010 | Rockway et al. |
| 7,799,772 B2 | 9/2010 | Freyne et al. |
| 7,960,546 B2 | 6/2011 | Schroeder et al. |
| 8,143,276 B2 | 3/2012 | Yang et al. |
| 8,148,532 B2 | 4/2012 | Chen |
| 8,212,033 B2 | 7/2012 | Su et al. |
| 8,232,294 B2 | 7/2012 | Xi |
| 8,349,857 B2 | 1/2013 | Kumes et al. |
| 8,394,786 B2 | 3/2013 | Freyne et al. |
| 8,404,697 B2 | 3/2013 | Solca et al. |
| 8,492,560 B2 | 7/2013 | Stokes et al. |
| 8,575,203 B2 | 11/2013 | Englehardt et al. |
| 8,618,289 B2 | 12/2013 | Abraham et al. |
| 8,642,767 B2 | 2/2014 | Spinelli et al. |
| 8,673,929 B2 | 3/2014 | Gao et al. |
| 9,169,236 B2 | 10/2015 | Fontana et al. |
| 9,353,122 B2 | 5/2016 | Ong et al. |
| 9,382,232 B2 | 7/2016 | Gong et al. |
| 9,637,484 B2 | 5/2017 | Peng et al. |
| 9,853,396 B1 | 12/2017 | Musick |
| 2003/0092721 A1 | 5/2003 | Pitts et al. |
| 2003/0191308 A1 | 10/2003 | Hennequin et al. |
| 2005/0009815 A1 | 1/2005 | Devita et al. |
| 2005/0085465 A1 | 4/2005 | Hennequin |
| 2006/0069077 A1 | 3/2006 | Rice et al. |
| 2007/0027318 A1 | 2/2007 | Kubo et al. |
| 2008/0058342 A1 | 3/2008 | Hennequin |
| 2008/0096884 A1 | 4/2008 | Edin et al. |
| 2008/0207617 A1 | 8/2008 | Miwa et al. |
| 2008/0227812 A2 | 9/2008 | Chen |
| 2008/0280917 A1 | 11/2008 | Albrecht et al. |
| 2009/0053236 A1 | 2/2009 | Yamamoto |
| 2009/0069316 A1 | 3/2009 | Hong et al. |
| 2009/0131461 A1 | 5/2009 | Davidson et al. |
| 2009/0312313 A1 | 12/2009 | Shimizu et al. |
| 2010/0022586 A1 | 1/2010 | Govek et al. |
| 2010/0144639 A1 | 6/2010 | Singer et al. |
| 2010/0234324 A1 | 9/2010 | Eggenweiler et al. |
| 2011/0269758 A1 | 11/2011 | Xiao et al. |
| 2012/0129877 A1 | 5/2012 | Martinez et al. |
| 2012/0142929 A1 | 6/2012 | Patel et al. |
| 2012/0238587 A1 | 9/2012 | Lee et al. |
| 2013/0079342 A1 | 3/2013 | Dransfield et al. |
| 2013/0345258 A1 | 12/2013 | Bury et al. |
| 2014/0221402 A1 | 8/2014 | Lu et al. |
| 2014/0221405 A1 | 8/2014 | Scarborough et al. |
| 2014/0275129 A1 | 9/2014 | Lee et al. |
| 2015/0057263 A1 | 2/2015 | Brown et al. |
| 2015/0329498 A1 | 11/2015 | Romero et al. |
| 2016/0060249 A1 | 3/2016 | Casillas et al. |
| 2016/0101106 A1 | 4/2016 | Werner |
| 2016/0108035 A1 | 4/2016 | Peng et al. |
| 2016/0297775 A1 | 10/2016 | Zhang |
| 2017/0035761 A1 | 2/2017 | Alami et al. |
| 2017/0174703 A1 | 6/2017 | Wu et al. |

FOREIGN PATENT DOCUMENTS

| | | |
|---|---|---|
| CN | 103298460 A | 9/2013 |
| CN | 104193728 A | 12/2014 |
| EP | 0326328 A2 | 8/1989 |
| EP | 326329 A2 | 8/1989 |
| EP | 0326329 A2 | 8/1989 |
| EP | 326330 A2 | 8/1989 |
| EP | 0414386 A1 | 2/1991 |
| EP | 1409481 A1 | 5/1992 |
| EP | 520722 A1 | 12/1992 |
| EP | 566226 A1 | 10/1993 |
| EP | 635498 A1 | 1/1995 |
| EP | 635507 A1 | 9/1999 |
| EP | 2268623 A1 | 1/2011 |
| EP | 2445886 A1 | 5/2012 |
| EP | 2522658 A1 | 11/2012 |
| EP | 3012251 A1 | 4/2016 |
| WO | 1990005523 A2 | 5/1990 |
| WO | 1992017452 A1 | 10/1992 |
| WO | 1992022533 A1 | 12/1992 |
| WO | 9404526 A1 | 3/1994 |
| WO | 1994004527 A1 | 3/1994 |
| WO | 1996009294 A1 | 3/1996 |
| WO | 1996039145 A1 | 12/1996 |
| WO | 1997003069 A1 | 1/1997 |
| WO | 1998013350 A1 | 4/1998 |
| WO | 1998043960 A1 | 10/1998 |
| WO | 9931072 A1 | 6/1999 |
| WO | 2000068199 A1 | 11/2000 |
| WO | 2000068200 A1 | 11/2000 |
| WO | 2000068201 A1 | 11/2000 |
| WO | 2001021596 A1 | 3/2001 |
| WO | 2001046150 A2 | 6/2001 |
| WO | 2002018375 A1 | 3/2002 |
| WO | 2002020489 A2 | 3/2002 |
| WO | 2003047582 A1 | 6/2003 |
| WO | 2003047583 A1 | 6/2003 |
| WO | 2003047585 A1 | 6/2003 |
| WO | 2003048159 A1 | 6/2003 |
| WO | 2003053960 A2 | 7/2003 |
| WO | 2003055866 A1 | 7/2003 |
| WO | 2005058318 A1 | 6/2005 |
| WO | 2003047584 A1 | 6/2006 |
| WO | 2006108059 A1 | 10/2006 |
| WO | 2006121767 A2 | 11/2006 |
| WO | 2007055513 A1 | 5/2007 |
| WO | 2008024423 A2 | 2/2008 |
| WO | 2009010139 A2 | 1/2009 |
| WO | 2009024611 A2 | 2/2009 |
| WO | 2009148659 A2 | 12/2009 |
| WO | 2010018555 A2 | 2/2010 |
| WO | 2010025451 A2 | 3/2010 |
| WO | 2011014039 A1 | 2/2011 |
| WO | 2011143444 A2 | 11/2011 |
| WO | 2012080727 A2 | 6/2012 |
| WO | 2012090179 A2 | 7/2012 |
| WO | 2013012915 A1 | 1/2013 |
| WO | 2013074633 A1 | 5/2013 |
| WO | 2014043437 A1 | 3/2014 |
| WO | 2014183555 A1 | 11/2014 |
| WO | 2015079067 A2 | 6/2015 |
| WO | 2015079251 A1 | 6/2015 |
| WO | 2015106025 A1 | 7/2015 |
| WO | 2015144001 A1 | 10/2015 |
| WO | 2015155262 A1 | 10/2015 |

OTHER PUBLICATIONS

Harsora, Synthesis, Characterization and Antimicrobial Screening of Some Bio-active Heterocyclic Compounds, Maharaja Krishnakumarsinhji Bhavnagar University Thesis, Jan. 2011, Part I, 26-88.

Kumar, Studies on Diversity Oriented synthesis of Bioactive Compounds, Jawaharlal Nehru University Thesis, Jun. 2009, Chaper 1, 1-27.

(56) References Cited

OTHER PUBLICATIONS

Pubchem, CID 23631972, Jan. 3, 2008, pp. 1-11. Retrieved from the Internet <URL: https://pubchem.ncbl.nlm.nih.gov/compound/236319721972>.
Pubchem, CID 616883, Mar. 27, 2005, pp. 1-14. Retrelved from the Internet <URL: https://pubchem.nal.nlm.nlh.gov/compound/616883>.
Pubchem, CID 21002400, Dec. 5, 2007, pp. 1-10. Retreived from the Internet <URL: https://pubchem.ncbi.nlm.nih.gov/compound/21002400>.
International Search Report and Written Opinion, from the International Searching authority, in Int. App. No. PCT/US16/55561, dated Mar. 27, 2017.
Pubchem, CID 640956, Jan. 25, 2006, Retrieved from the internet <URL https://pubchem.ncbi.nlm.nih.gov/compound/640956>.
Pubchem, CID 57263900, Jun. 15, 2012, Retrieved from the internet <URLhttps://pubchem.ncbi.nlm.nih.gov/compound/57263900>.
International Search Report and Written Opinion, from the International Searching authority, in Int. App. No. PCT/US17/54969, dated Jan. 18, 2018.
PubChem, CID 88934329, retrieved from the Internet <URL: https://pubchem.ncbi.nlm.nih.gov/compound/88934329> (record date, Feb. 13, 2015).
Supplementary European Search Report in European Application No. 16854245.4, dated Mar. 19, 2019.
Chemical Reactions, Benha University Thesis, Chapter Synthesis of 4-(3H)-quinazolinones from Anthranilic Acid or its Derivatives.
PubChem, CID 88934329, retrieved from the internet<URL:https://pubchem.ncbi,nim,nih,gov/compund/88934329. (record date, Feb. 13, 2015).
Byju et al., Therapeutic Potential of Quinazoline and its Derivatives—A Review, International Journal of Institutional Pharmacy and Life Sciences 5(2): Mar.-Apr. 2015.
Ajani et al., Quinazoline Pharmacophore in Therapeutic Medicine, Bangladesh J Pharmacol 2016; 11: 716-733.
Alam et al., A Review. Recent Investigations on Quinazoline Scaffold, International Journal of Advance Research (2015), vol. 3, Issue 12, 1656-1664.
Wang et al., Quinazoline Derivatives: Synthesis and Bioactivities, Chemistry Central Journal 2013, 7:95.
Chandrika et al., Synthesis Leading to Novel 2,4,6 Trisubstituted Quinazoline Derivatives, their Antibacterial and Cytotoxic Activity against THP-1, HL-60 and A375 Cell Lines, Indian Journal of Chemistry, vol. 48B, Jun. 2009, 340-847.
El-Azab et al., Design, Synthesis and Biologica Evaluation of novel Quinazofine Derivatives as Potential Antitumor Agents: Molecular Docking Study, European Journal of Medicinal Chemistry, vol. 45, Issue 9, Sep. 2010, 1188-4198.
Chao et al., Substituted Isoquinolines and Quinazolines as Potential Antiinfiammatory Agents. Synthesis and Biological Evaluation of Inhibitors of Tumor Necrosis Factor a, Journal of Medicinal Chemistry, 1999, 42 (19), 3860-3873.
German et al., Use of Gyrase Resistance Mutants to Guide Selection of 8-Methoxy-Quinazoline-2,4-Diones, American Society for Microbiology, vol. 52, No. 11, Nov. 2008, 3915-3921.
Naga Raju et al., Quinazoline: Unique and Versatile Pharmacophore in the field or Cancer, Indo American Journal of Pharmaceutical Sciences, 2015, vol. 2 (4), 827-832.
Asif, Chemical Characteristics, Synthetic Methods, and Biological Potential of Quinazoline and Quinazolirtone Derivatives, International Journal of Medicinal Chemistry, vol. 2014, Article ID 395637.
Jafari et al. Quinazolinone and Quinazoline Derivatives: Recent Structures with Potent Antimicrobial and Cytotoxic Activities, Research in Pharmaceutical Sciences, Jan.-Feb. 2016. 11(1): 1-14.
Xu, Synthesis and Antifungal Activity of Novel s-Substituted 6-fluoro-4-alkyl(aryl)thioquinazoline Derivatives, Bioorganic & Medicinal Chemistry 15, Mar. 2007, 3768-3774.
Babu, Synthesis, Characterization and Biological Evaluation of Novel Tri Substituted Quinazoline-isatin Mannich Basses Bearing Morpholine and Biphenyl Moieties, Hetrocyclic Letters, May-Jul. 2015, vol. 5, No. 3, 395-411.

Al-Salahi, Synthesis of Novel 2-Alkoxy(aralkoxy)-4H-[1,2,4]triazolo11,5-a] quinazolin-5-ones and Derivatives, University of Hamburg, Jan. 23, 2009.
El-Sakka et al., Synthesis and Biological Activity of Nitrogen Heterocycles From Anthranilic Acid Derivative, Oriental Journal of Chemistry, May 6, 2009, vol. 25(2), 287-294.
Prajapati et al., Synthesis and Preliminary in-vitro Cytotoxic Activity of Morpholino Propoxy Quinazoline Derivatives, International Journal of ChemTech Research, Jan.-Mar. 2014, vol. 6, No. 1, 547-555.
Diab et al., Radiation Dosimetric Properties of New Oxa-, Thiadiazole, Tilazote, International Journal of Physics and Research, Dec. 2013, vol. 3, Issue 5, 11-20.
Aman et al., QSAR Study of Quinazoline Derivatives as Inhibitor of Epidermal Growth Factor Receptor-Tyrosine Kinase (EGFR-TK), 3rd International Conference on Computation for Science and Technology, Nov. 30, 2014.
Chandrika et al., Quinazoline Derivatives with Potent Anti-Inflammatory and Anti-Allergic Activities, Int. J. Chem. Sci., 2008, 6(3), 1119-1146.
Manjula et at., Medicinal and Biological Significance of Quinazoline: A Highly Important Scaffold for Drug Discovery: A Review, International Journal of Pharma and Bio Sciences, Jan.-Mar. 2011, vol. 2, Issue 1, 780-809.
Connolly, Synthesis of Quinazolinones and Quinazofines, Tetrahedron 61, Jun. 2005, Report No. 737, 10153-10202.
Jantova et al., In Vitro Antibacterial Activity of Ten Series of Substituted Quinazolines, Biologia, Bratislava, 2004, 59/6, 741-752.
Barclay et al, Quinolines as Chemotherapeutic Agents for Leishmaniasis, Griffith University, 2013.
Selvam et al., Quinazoline Marketed Drugs—A Review, Research in Pharmacy, 2011, 1(1), 1-21.
Wan et al, Synthesis, Antiviral Bioactivity of Novel 4-Thioquinazoline Derivatives Containing Chalcone Moiety, Molecules, Jun. 2015, 20, 11861-11874.
El-Hashash et al., Synthesis and Evaluation of New 2,3- and 2,4-Disubstituted Quinazoline Derivatives As Potential Antibacterial and Antifungal Agents, Scholars Research Library, Der Pharma Chemica, 2011, 3(6), 147-159.
Sahu et al., in Silico Screening, Synthesis and In Vitro Evaluation of Some Quinazolinone Derivatives As Dihydrofolate Reductase Inhibitors for Anticancer Activity, International Journal of Pharmacy and Pharmaceutical Sciences, Mar. 2014, vol. 6, Issue 5, 193-199.
Lynch et al., 4-Aminoquinolines as Antimalarial Drugs, Trinity Student Scientific Review vol. II, 2016 Edition, 196-211.
Rudrapal et al., Novel 4-Aminoquinoline Analogues As Antimalarial Agents: A Review, Scholars Research Library, Der Phamacia Letter, 2011, 3(3), 29-36.
Kuldeep et al., Review of Synthesis Schemes of Some Biological Active Quinolines, International Journal of Pharmacotherapy, 2015, 5(2), 75-79.
Odingo et al., Synthesis and Evaluation of the 2,4-Diaminoquinazoline Series as Anti-Tubercular Agents, Biorganic & Medicinal Chemistry 22 (2014) 6965-6979.
Dassonville-Klimpt et al., Mefloquine Derivatives : Synthesis, Mechanisms of Action, Antimicrobial Activities, Universite de Picardie Jule Verne, 2011.
Xie et al., Synthesis of Nitrogen-Containing Heterocycles Using Nitro Compounds as Building Blocks: Part I: Synthesis of 3-Substituted Azepanes. Part II: Synthesis of 1-Azoniapropellanes as Phase Transfer Catalysts, University of Illinois at Urbana-Champaign, 2010.
Viart et al., Synthesis and Structure-Activity Relationship of Uposomal Substrates for Phospholipase A(2), Absracts )f Papers of the American Chemical Society, 2011, 242, Medi 344.
Dow et al., Utility of Alkylaminoquinolinyl Methanols As New Antimalarial Drugs, Antimicrobial Agents and Chemotherapy, Dec. 2006, vol. 50, No. 12, 4132-4143.
Marella et al., Quinoline: A Versatile Heterocyclic, King Saud University, Saudi Pharmaceutical Journal, Mar. 2012, 21-12.

(56) References Cited

OTHER PUBLICATIONS

Poonan et al., A Review on Biological Activities of Quinoline Derivatives, Journal of Management Information Technology and Engineering, Jun. 2016, vol. 2, Issue 1, 1-14.
Yang, Discovery of Selective Histone Deacetylase 6 Inhibitors Using the Quinazoline as the Cap for the Treatment of Cancer, Journal of Medical Chemistry, Oct. 2015, 59(4), 1455-1470.
Duan, Synthesis and Evaluation of (2-(4-Methoxyphenyl)-4-quinolinyl) (2-piperidinyl)methanol (NSC23925) Isomers to Reverse Multidrug Resistance in Cancer, Journal of Medicinal Chemistry, Mar. 2012, 55, 3113-3121.
Pubchem, CID 21002494, Retrieved from the Internet <URL https://pubchem.ncbi.nlm.nih.gov/compound/21002494#section-Chemical-Vendors>.
Pubchem, CID 44428806, Retrieved from the Internet <URL: https://pubchem.ncbi.nlm.nih.gov/compound/4428806itsection=Top>.
Guidechem, 4(3H)-Quinazolinethione,2-methyl-(CAS No. 648428-2), Retrieved from the Internet <URL: http://guidechem.com/reference/dic-168980>.
Shah, Synthesis and Biological Evaluation of Certain Nitrogen and Sulfur Based Bioactive Scaffolds, Gujarat University Thesis, Chapter 1, 2014.
ChemFuture Catalog Products 2010, ChemFuture PharmaTech (China) Ltd.
4-(furan-2-ylmethylsulfanyl)quinazoline, Henan Coreychem Co.,Ltd, 2012, Retrieved from the Internet <URL http://coreychem.com/PRODUCTS/Phamaceutical_intermediates/2015/05231/195760.html>.
Pubchem, CID 7160394, Retrieved from the Internet <URL: https://pubchem.ncbi.nlm.nth.gov/compound/7160394#section-Top>.
Pubchem, CID 60329852, Retrieved from the Internet <URL: https://pubchem.ncbi.nlm.nih.gov/compound/60329852/#section=2D-Structure>.

A. Rinderspacher, et al., "Potent Inhibitors of Huntingtin Protein Aggregation in a Cell-Based Assay", Bioorg Med Chem Lett., 19(6), pp. 1715-1717 (2009).
R. Saari, et al., "Microwave-assisted synthesis of quinoline, isoquinoline, quinoxaline and quinazoline derivatives as CB2 receptor agonists", Bioorganic & Medicinal Chemistry, 19, pp. 939-950 (2011).
B. Hu, et al., "Hexachlorocyclotriphosphazene (HCCP)-Mediated Direct Formation of Thioethers and Ethers from Quinazolin-4(3H)-ones", Molecules, 18, pp. 5580-5593 (2013).
S. Radl, et al., "Synthesis and Analgesic Activity of Some Quinazoline Analogs of Anpirtoline", Arch. Pharm. Med. Chem., 333, pp. 381-386 (2000).
S. Yang, et al., "Synthesis and bioactivity of 4-alkyl(aryl)thioquinazoline derivatives", Bioorganic & Medicinal Chemistry Letter, 17, pp. 2193-2196 (2007).
CAS Registry; RN:1523031-22-2, Entered on Jan. 17, 2014.
CAS Registry; RN:1274044-98-2, Entered on Apr. 3, 2011.
CAS Registry; RN:1153094-45-1, Entered on Jan. 7, 2009.
CAS Registry; RN:1097030-29-9, Entered on Jan. 28, 2009.
CAS Registry; RN:1401991-13-6, Entered on Oct. 24, 2012.
CAS Registry; Rn: 929503-36-6, Entered on Apr. 9, 2007.
CAS Registry; RN:929370-68-3, Entered on Apr. 8, 2007.
Kaslow, C.E., et al., "Substituted Phenylquinolines", Journal of Organic Chemistry, vol. 20, No. 12, pp. 1738-1742 (1995).
Apelt, J., et al., "Development of a New Class of Nonimidazole Histamine H3 Receptor Ligands with Combined Inhibitory Histamine N-Methyltrnsferase Activity", Journal of Medicinal Chemistry, vol. 45, No. 5, pp. 1128-1141 (2002).
RN: 1553718-81-2, 1553722-63-6, ACS, STN Registry database.
RN: 126992-02-7, ACS, STN Registry database.
Xiong, H., et al., "Facile Route to 2-Fluoroprdines via 2-Pyridyltrialkylammonium Salts Prepared from Pyridine N-Oxides and Application to F-Labeling", Organic Letters, vol. 17, No. 15, pp. 3726-3729 (2015).

* cited by examiner

ACTIVATORS OF AUTOPHAGIC FLUX AND PHOSPHOLIPASE D AND CLEARANCE OF PROTEIN AGGREGATES INCLUDING TAU AND TREATMENT OF PROTEINOPATHIES

CROSS-REFERENCE TO RELATED APPLICATIONS

The present application is a division of U.S. patent application Ser. No. 15/480,220 filed Apr. 5, 2017, published as US 2017/0210759, which is a Continuation-in-Part (CIP) application that claims benefit to International Application Serial No. PCT/US16/055561, filed Oct. 5, 2016, published as WO 2017/062500, which International Application claims benefit to U.S. Provisional Application Ser. No. 62/237,342, filed Oct. 5, 2015. The entire contents of the above aforementioned applications are incorporated by reference as if recited in full herein.

FIELD OF THE DISCLOSURE

The present disclosure relates to compounds which are activators of autophagic flux and pharmaceutical compositions comprising said compounds. It further relates to use of said compounds in the treatment of neurodegenerative diseases, particularly Alzheimer's disease.

BACKGROUND OF THE INVENTION

Alzheimer's disease (AD) affects approximately five million Americans and this number is predicted to triple by 2050. At present, there are no therapies to treat Alzheimer's or other related tauopathies. While clinical trials using immunotherapy targeting amyloid beta (Aβ) have had limited success, this in only subset of those afflicted with AD or other neurodegenerative diseases. Moreover, there are no therapies targeting other proteinopathies, including tau, the other major neuropathological component of AD. AD accounts for most of the dementias afflicting individuals over 65 and is estimated to cost $226 billion in healthcare, long-term care, and hospice for people with AD and other dementias annually. This extensive economic and societal burden does not account for lost income of many at-home primary caregivers including spouses and other family members.

Enhancing autophagy has been shown to have therapeutic potential in the treatment of Alzheimer's disease. Autophagic flux (including the fusion of autophagosomes to lysosomes) is a novel regulator of autophagy as it leads to the clearance of protein aggregates and reversal of pathophysiological decline. Therefore, there exists an ongoing need for promoters of autophagic flux and the clearance of autophagosomes bearing proteinopathies.

SUMMARY OF THE INVENTION

In some embodiments, compounds including pharmaceutically acceptable salts thereof, which are disclosed herein, are provided.

In some embodiments a pharmaceutical composition is provided comprising a compound disclosed herein or a pharmaceutically acceptable salt thereof. In other embodiments, methods of making the compounds and pharmaceutical compositions are also provided in, e.g., the Examples provided below.

In some embodiments a method of treating a neurodegenerative disease comprising administering to a subject in need thereof an effective amount of a compound or pharmaceutical composition disclosed herein is provided.

In some embodiments a method of enhancing autophagic flux is provided. This method comprises providing to a cell or a protein aggregate an effective amount of a compound or pharmaceutical composition disclosed herein.

These and other aspects of the invention are furtherdisclosed in the detailed description and examples which follow.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
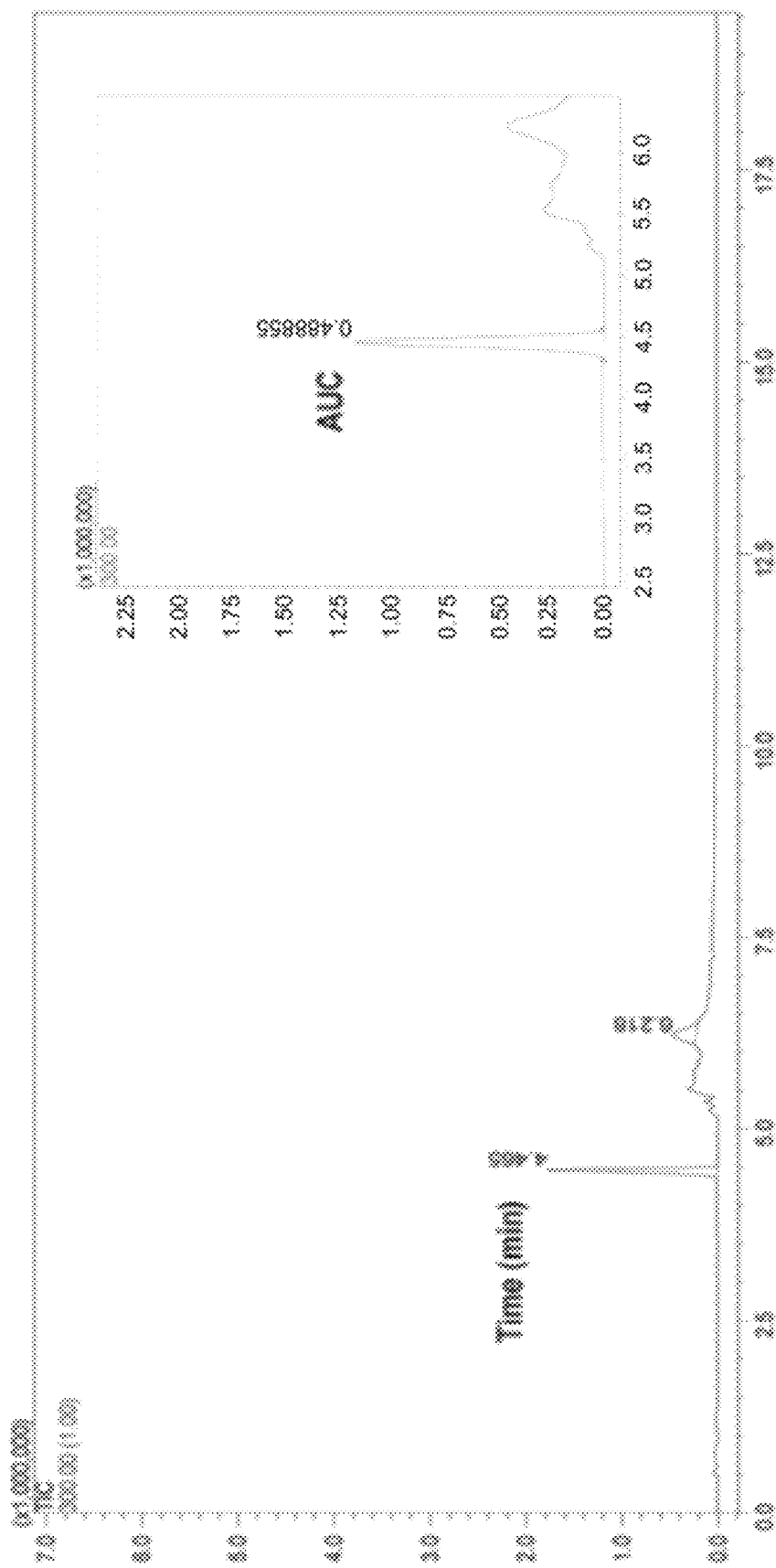
FIG. 1 is a graph showing a photodiode array (PDA) spectrum of WHYKD8 in mouse brain.

Although macroautophagy is known to be an essential degradative process whereby autophagosomes mediate the engulfment and delivery of cytoplasmic components into lysosomes, the lipid changes underlying autophagosomal membrane dynamics are undetermined. The inventors have previously shown that PLD1, which is primarily associated with the endosomal system, partially relocalizes to the outer membrane of autophagosome-like structures upon nutrient starvation (Dall'Armi, 2010). The localization of PLD1, as well as the starvation-induced increase in PLD activity, are altered by wortmannin, a phosphatidylinositol 3-kinase inhibitor, suggesting PLD1 may act downstream of Vps34. Pharmacological inhibition of PLD and genetic ablation of PLD1 in mouse cells decreased the starvation-induced expansion of LC3-positive compartments, consistent with a role of PLD1 in the regulation of autophagy. Furthermore, inhibition of PLD results in higher levels of tau and p62 aggregates in organotypic brain slices. These in vitro and in vivo findings establish a role for PLD1 in autophagy.

In some embodiments, a compound is provided having the formula (II):

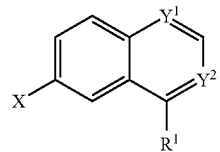

wherein Y¹ and Y² are independently selected from the group consisting of CH and N;
wherein X is selected from the group consisting of H, halide, and aryl;
wherein R¹ is selected from the group consisting of optionally substituted thioheteroaryl, hydroxyl-substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl,
or a salt, enantiomer, racemate, mixture thereof, or combination thereof.

In some embodiments, the compound is selected from the group consisting of:

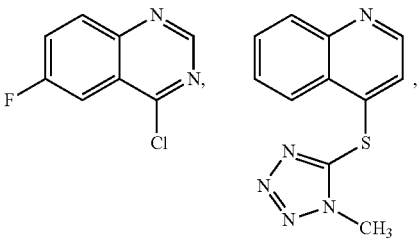

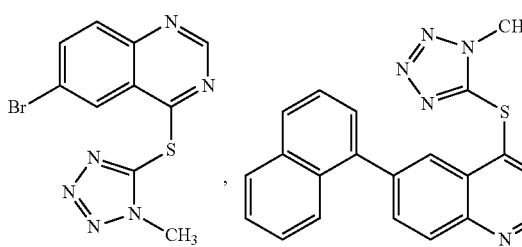

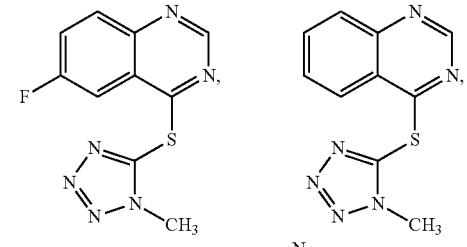

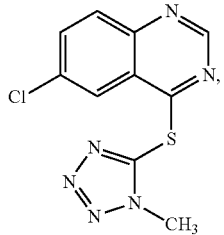

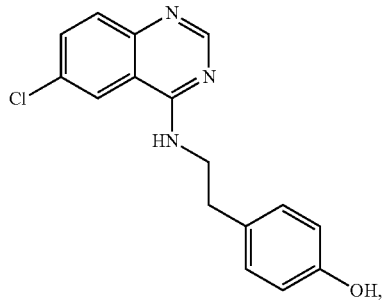 [SMILES: Oc1ccc(CCNc2ncnc3ccc(Cl)cc23)cc1]

-continued

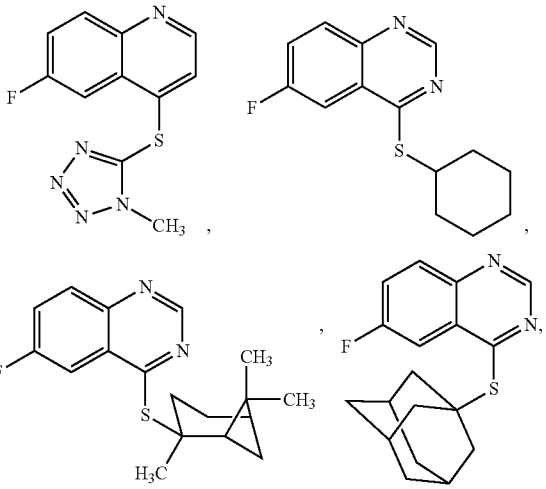

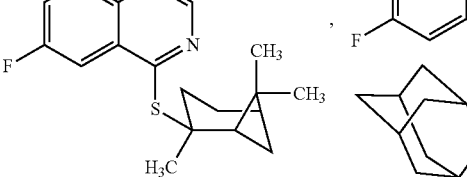

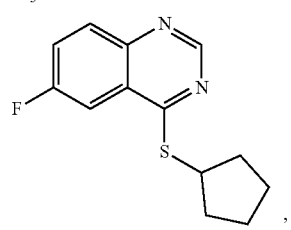

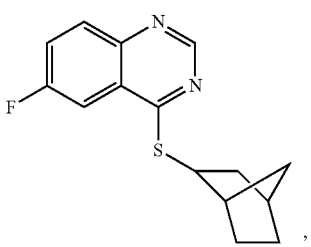

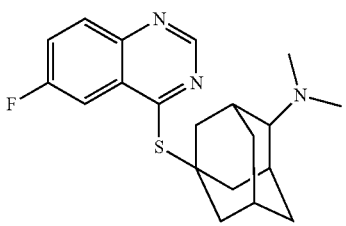

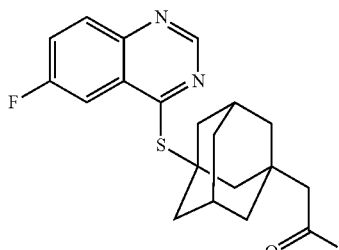

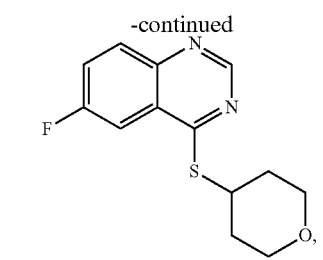
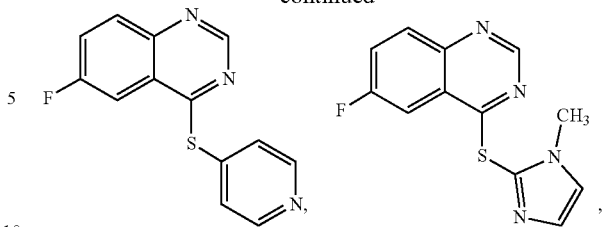
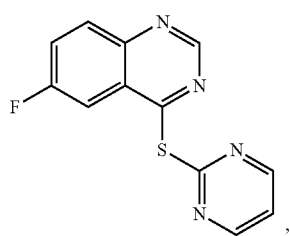
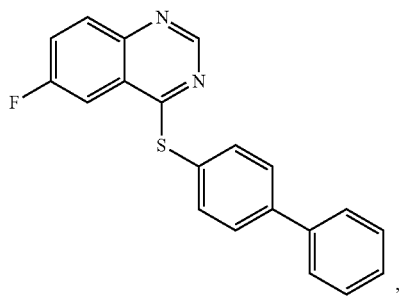
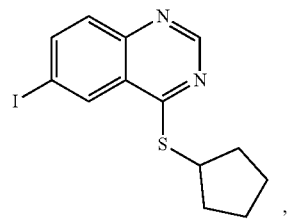
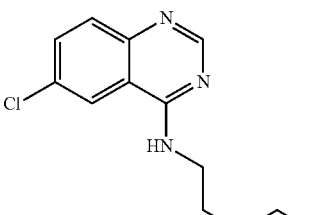
or a salt, enantiomer, racemate, mixture thereof, or combination thereof.
In one embodiment the compound is:
or a salt, enantiomer, racemate, mixture thereof, or combination thereof.

In another embodiment the compound is:

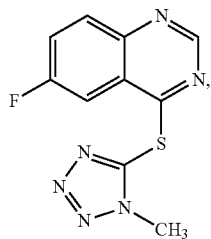

or a salt, enantiomer, racemate, mixture thereof, or combination thereof.

In some embodiments, a compound is provided having the formula (III):

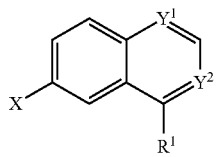

wherein $Y^1$ is CH;
wherein $Y^2$ is N;
wherein X is halide;
wherein $R^1$ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl,
or a salt, enantiomer, racemate, mixture thereof, or combination thereof.

In some embodiments, the compound is selected from the group consisting of:

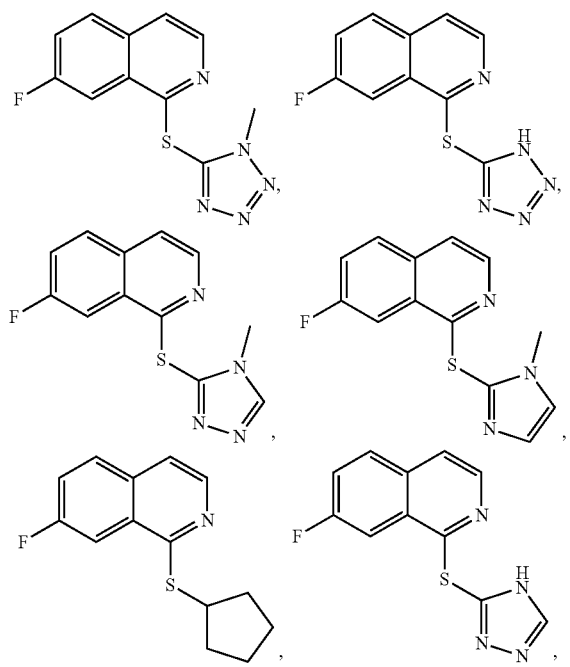

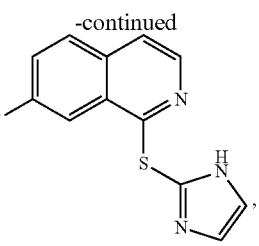

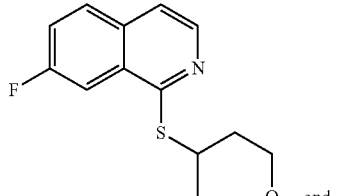

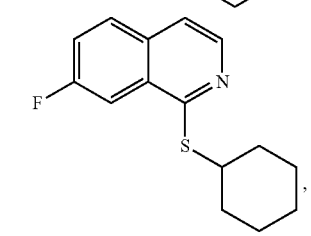

or a salt, enantiomer, racemate, mixture thereof, or combination thereof.

In some embodiments, a compound is provided having the formula (IV):

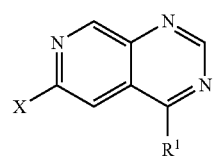

wherein X is halide;
wherein $R^1$ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl,
or a salt, enantiomer, racemate, mixture thereof, or combination thereof.

In some embodiments, the compound is selected from the group consisting of:

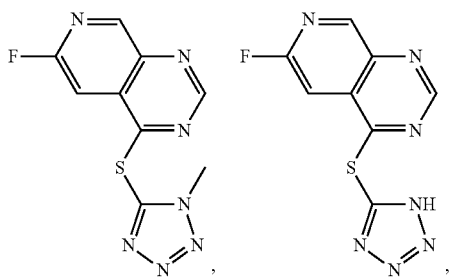

-continued

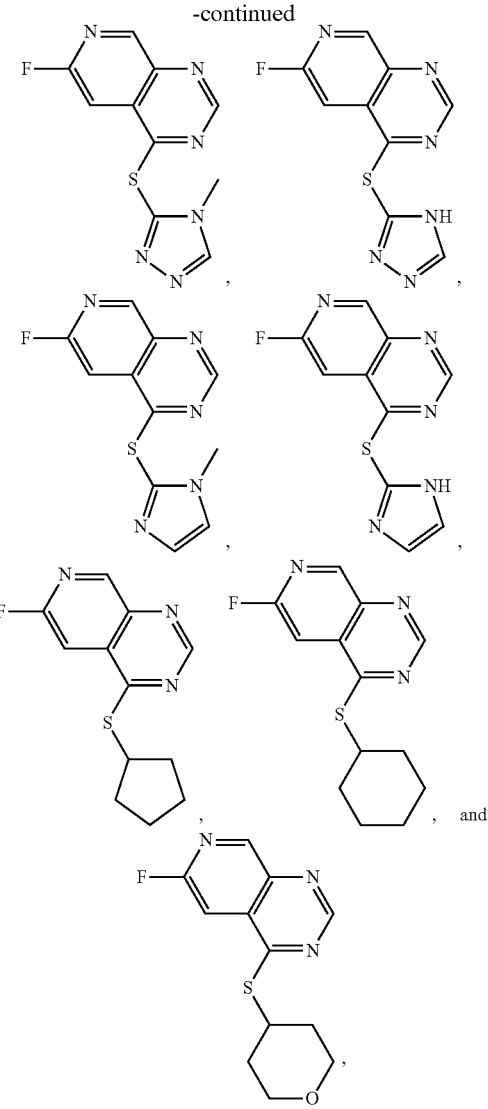

or a salt, enantiomer, racemate, mixture thereof, or combination thereof.

In some embodiments, a compound is provided having the formula (V):

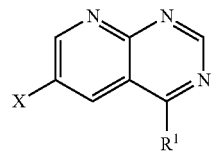

wherein X is H;
wherein R¹ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl,
or a salt, enantiomer, racemate, mixture thereof, or combination thereof.

In some embodiments, the compound is selected from the group consisting of:

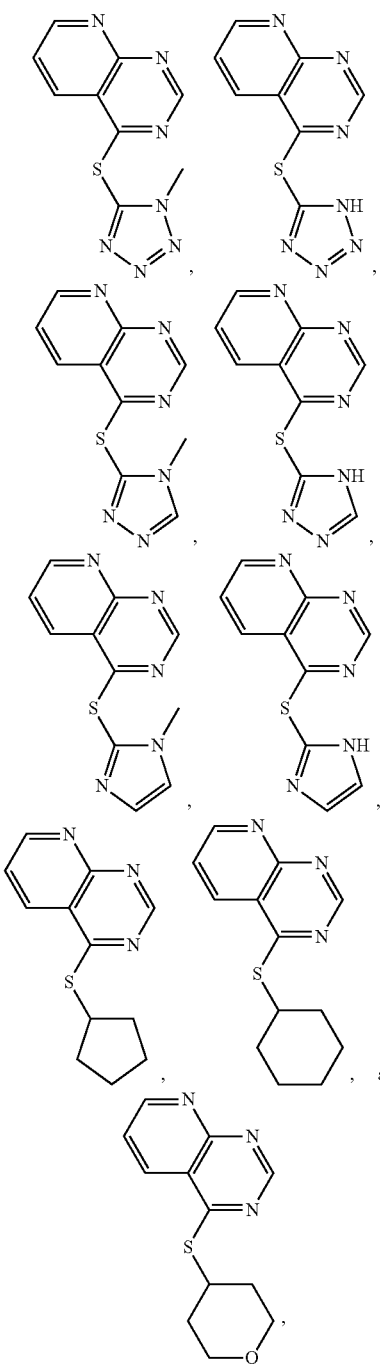

or a salt, enantiomer, racemate, mixture thereof, or combination thereof.

In some embodiments, a compound is provided having the formula (VI):

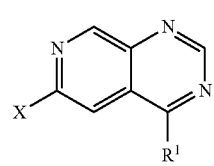

wherein X is H;
wherein R¹ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof.

In some embodiments, the compound is selected from the group consisting of:

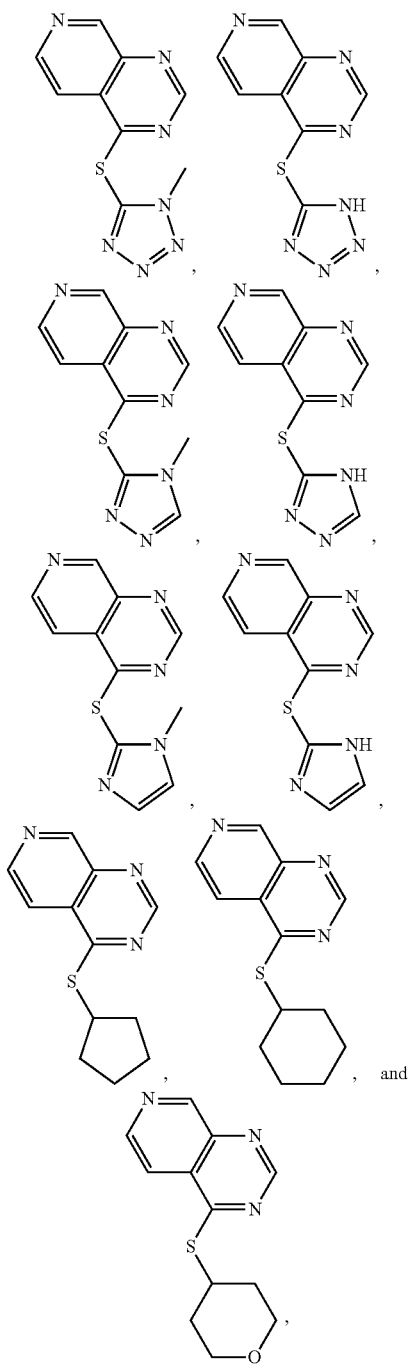

or a salt, enantiomer, racemate, mixture thereof, or combination thereof.

In some embodiments, a compound is provided having the formula (VII):

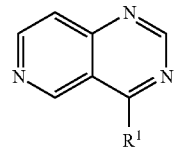

wherein R¹ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof.

In some embodiments, the compound is selected from the group consisting of:

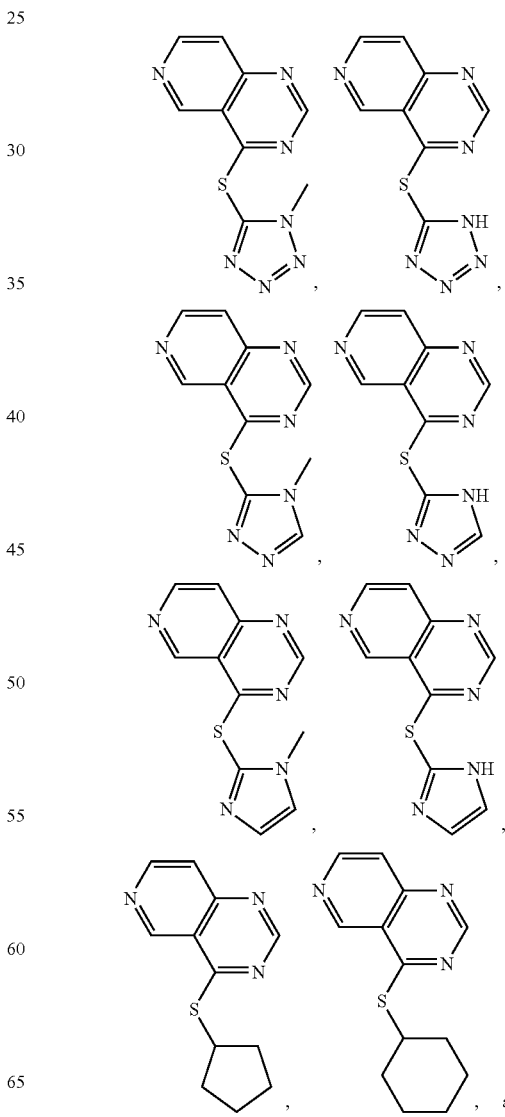

-continued

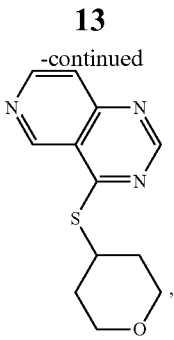

or a salt, enantiomer, racemate, mixture thereof, or combination thereof.

In some embodiments, a compound is provided having the formula (VIII):

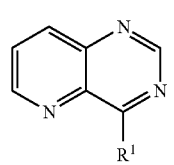

wherein $R^1$ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof.

In some embodiments, the compound is selected from the group consisting of:

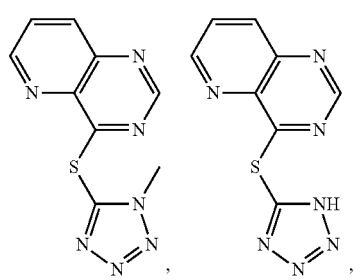

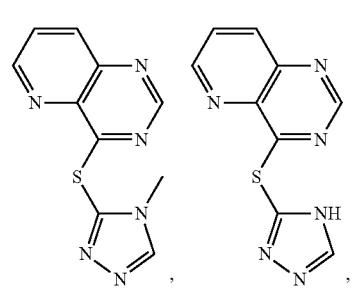

-continued

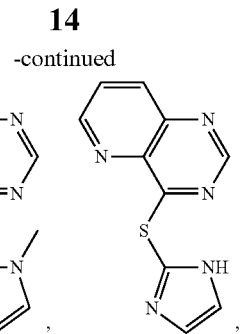

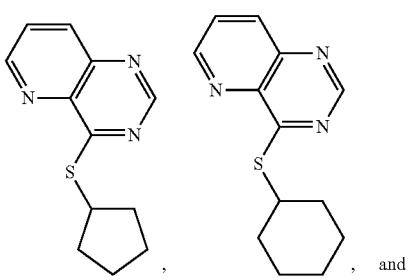

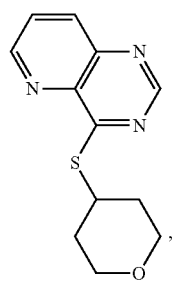

or a salt, enantiomer, racemate, mixture thereof, or combination thereof.

In some embodiments, a compound is provided having the formula (IX):

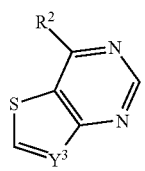

wherein $Y^3$ is CH or N;

wherein $R^2$ is optionally substituted (2-aminoethyl)aryl, or a salt, enantiomer, racemate, mixture thereof, or combination thereof.

In some embodiments, the compound is selected from the group consisting of:

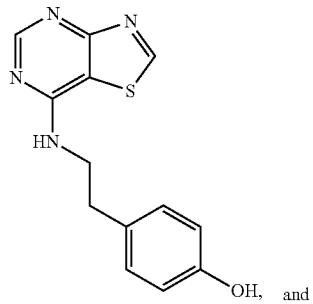 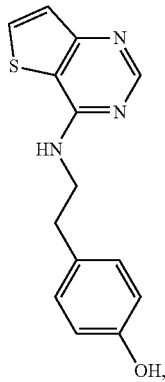

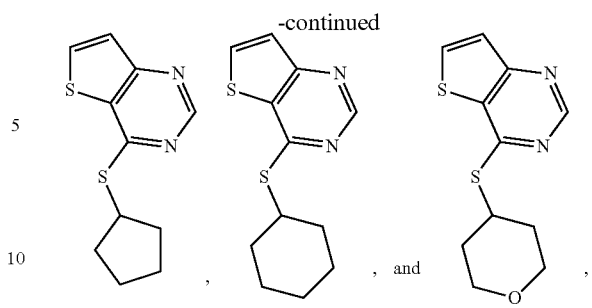

or a salt, enantiomer, racemate, mixture thereof, or combination thereof.

In some embodiments, a compound is provided having the formula (X):

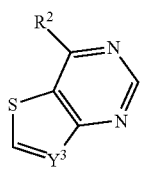

wherein $Y^3$ is CH;

wherein $R^2$ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof.

In some embodiments, the compound is selected from the group consisting of:

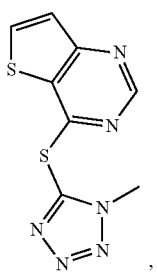 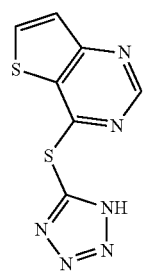 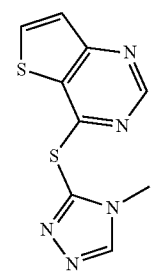

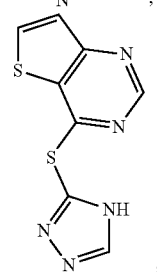 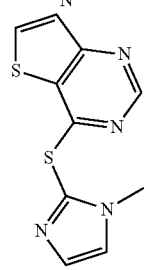 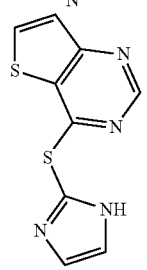

or a salt, enantiomer, racemate, mixture thereof, or combination thereof.

In some embodiments, a compound is provided having the formula (XI):

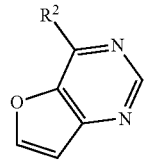

wherein $R^2$ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof.

In some embodiments, the compound is selected from the group consisting of:

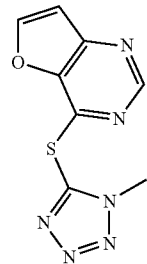 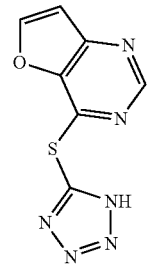 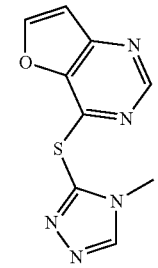

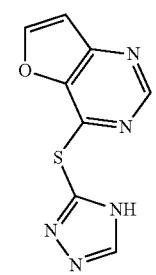 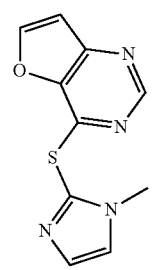 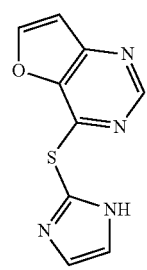

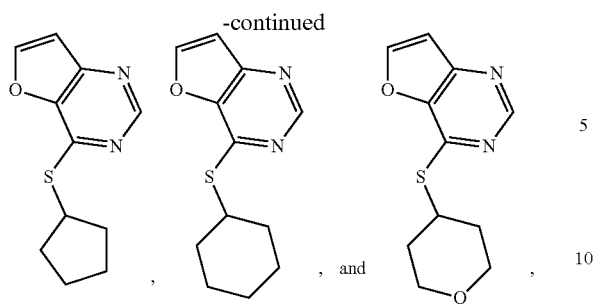

, and or a salt, enantiomer, racemate, mixture thereof, or combination thereof.

In some embodiments, a compound is provided having the formula (XII):

wherein Y⁴ is CH or N;

wherein $R^3$ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof.

In some embodiments, the compound is selected from the group consisting of:

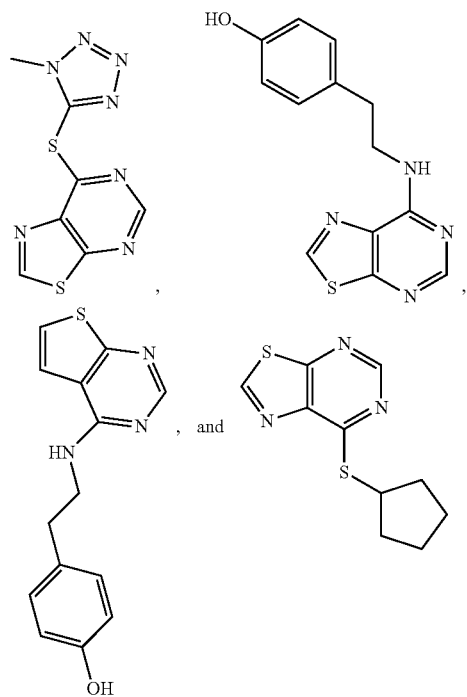

, and or a salt, enantiomer, racemate, mixture thereof, or combination thereof.

In some embodiments, a compound is provided having the formula (XIII):

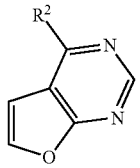

wherein $R^2$ is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof.

In some embodiments, the compound is selected from the group consisting of:

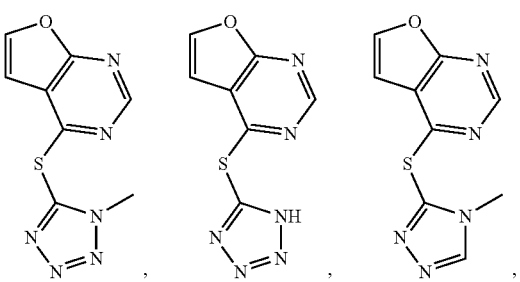

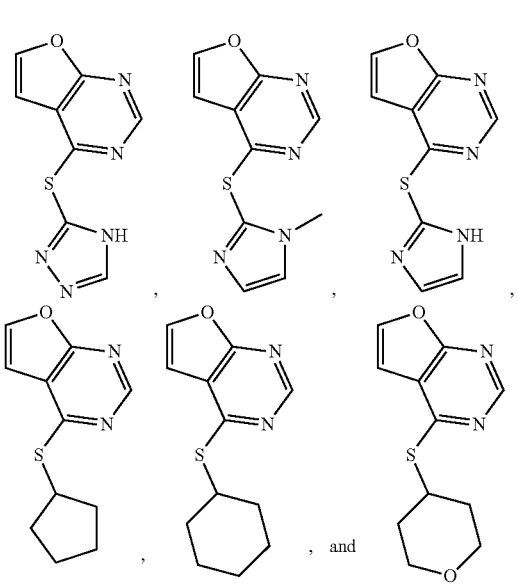

, and or a salt, enantiomer, racemate, mixture thereof, or combination thereof.

In some embodiments, a compound is provided having the formula (XIV):

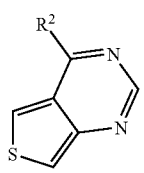

wherein R² is selected from the group consisting of optionally substituted thioheteroaryl, optionally substituted (2-aminoethyl)aryl, halide, optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof.

In some embodiments, the compound is selected from the group consisting of:

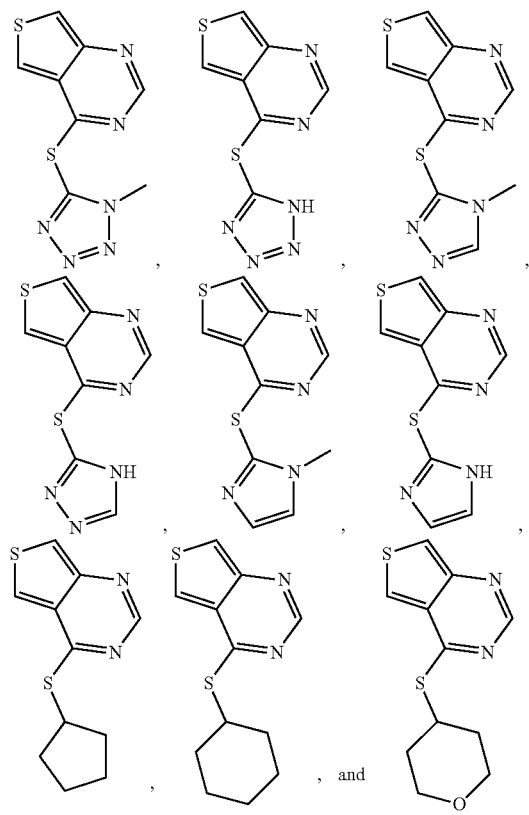

or a salt, enantiomer, racemate, mixture thereof, or combination thereof.

In some embodiments, a compound is provided having the formula (XV):

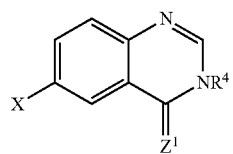

wherein X is H or halide;
wherein Z¹ is O;
wherein R⁴ is selected from the group consisting of H, optionally substituted alkyl, Et, CF₃, optionally substituted cycloalkyl, optionally substituted aryl, optionally substituted heteroaryl, and

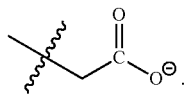 [SMILES: *CC(=O)[O-]]

In some embodiments, the compound is selected from the group consisting of:

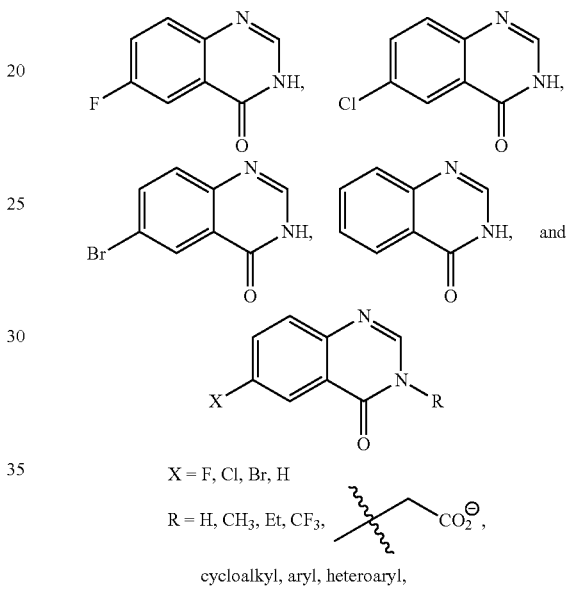

X = F, Cl, Br, H

R = H, CH₃, Et, CF₃, ⸺CO₂⁻, cycloalkyl, aryl, heteroaryl, or a salt, enantiomer, racemate, mixture thereof, or combination thereof.

In one embodiment the compound is

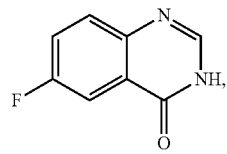

or a salt, enantiomer, racemate, mixture thereof, or combination thereof.

In some embodiments a pharmaceutical composition is provided comprising a compound disclosed herein or a pharmaceutically acceptable salt thereof.

In some embodiments a method of treating a neurodegenerative disease comprising administering to a subject in need thereof an effective amount of a compound or pharmaceutical composition disclosed herein is provided. In some embodiments the neurodegenerative disease is a proteinopathy. Proteinopathies include, but are not limited to, Parkinson's disease, Alzheimer's disease, Amyotrophic Lateral Sclerosis (ALS), Huntington's disease, chronic traumatic encephalopathy (CTE), frontotemporal dementia (FTD), inclusion body myopathy (IBM), Paget's disease of bone (PDB), cerebral β-amyloid angiopathy, prion diseases, familial dementia, CADASIL, amyloidosis, Alexander disease, seipinopathies, type II diabetes, pulmonary alveolar proteinosis, cataracts, cystic fibrosis and sickle cell disease. In some aspects of this embodiment, the proteinopathy is a tauopathy. Tauopothies include but are not limited to, Alzheimer's disease, Parkinson's disease, Huntington's disease, progressive supranuclear palsy, chronic traumatic encephalopathy (CTE), frontotemporal dementia (FTS), Lytico-Bodig disease, subacute sclerosing panencephalitis, ganglioglioma, gangliocytoma, and argyrophilic grain disease. In a preferred embodiment, the neurodegenerative disease is Alzheimer's disease.

In some embodiments a method of enhancing autophagic flux is provided. This method comprises providing to a cell or a protein aggregate an effective amount of a compound or pharmaceutical composition disclosed herein.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes may be made by those skilled in the art without departing from the spirit of this disclosure. Those skilled in the art will appreciate that the inventive principles can be practiced in other than the described embodiments, which are presented for purposes of illustration and not limitation.

EXAMPLES

The following examples are provided to further illustrate certain aspects of the present invention. These examples are illustrative only and are not intended to limit the scope of the invention in any way.

Example 1

Example Synthetic Schemes

Scheme 1 shows the synthesis of compounds of the formula:

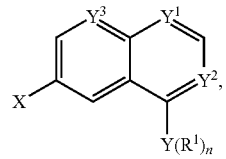

e.g., compounds of formula (II) and formula (III).

Scheme 1

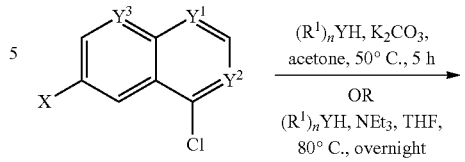

(R$^1$)$_n$YH, K$_2$CO$_3$, acetone, 50° C., 5 h

OR (R$^1$)$_n$YH, NEt$_3$, THF, 80° C., overnight

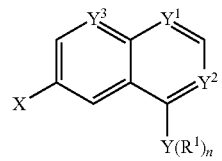

X = H, F, Cl, Br, I, CH$_3$, CF$_3$
Y = S, NH, N
Y$^1$ = CH, N
Y$^2$ = CH, N
Y$^3$ = CH, N
R$^1$ = H, alkyl, cycloalkyl, aryl, heteroaryl
n = 0, 1

Representative General Procedure

A 4-chloroquinazoline and thiol were stirred in anhydrous THF at room temperature. A base, such as triethylamine, was added. The reaction mixture was heated to 80° C. and was stirred overnight at said temperature, after which it was allowed to cool to room temperature. It was then diluted with distilled water, and the organic material was extracted with ethyl acetate (3×). The combined organic extracts were washed with brine (1×) and dried with anhydrous sodium sulfate. The solvent was evaporated in vacuo, and the crude material was purified either via column chromatography or prep TLC, employing either 10% MeOH in methylene chloride or 10:1 pentane:diethyl ether as the eluent.

The above procedure is representative. Other examples disclosed herein could be made by similar techniques or other methods known in the art.

Scheme 2 shows preparation of 1-chloro-7-fluoroisoquinoline.

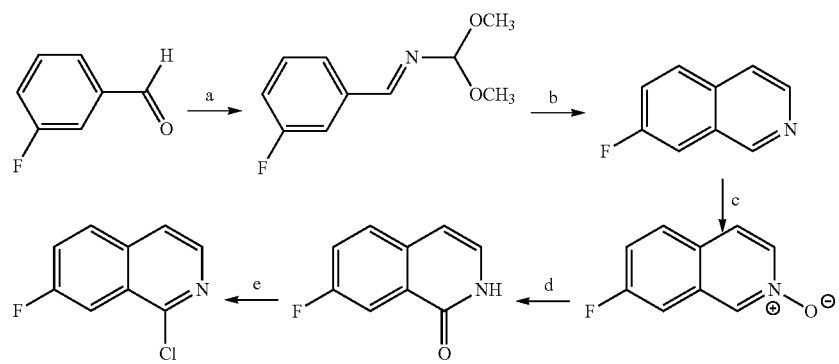

Reagents and conditions: a) aminoacetaldehyde dimethyl acetal, benzene, reflux; b) 1.) ClCO$_2$Et, -10° C., THF, 2.) P(OCH$_3$)$_3$, 3.) TiCl$_4$, CH$_2$Cl$_2$, reflux; c) H$_2$O$_2$, AcOH, 60° C.; d) 1.) Ac$_2$O, 2) NaOH; e) POCl$_3$, reflux Scheme 3 shows the synthesis of compounds of the formula:

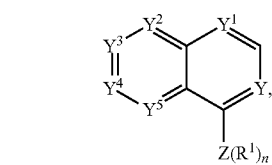

e.g., compounds of formula (IV), formula (V), formula (VI), formula VI and formula (VIII).

Scheme 3

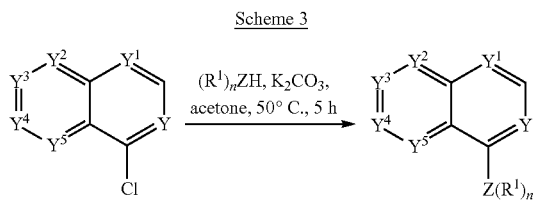

Y = CH, N
$Y^1$ = CH, N
$Y^2$ = CH, N
$Y^3$ = CH, N
$Y^4$ = CH, N
$Y^5$ = CH, N
Z = S, N, NH
$R^1$ = H, alkyl cycloalkyl, aryl, heteroaryl
n = 0, 1

Scheme 4 shows the synthesis of compounds of the formula:

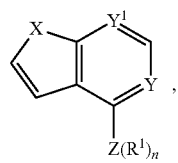

e.g., compounds of formula (XII), and formula (XIII).

Scheme 4

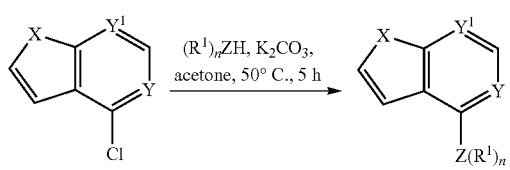

Y = CH, N
$Y^1$ = CH, N
Z = S, N, NH
$R^1$ = H, alkyl, cycloalkyl, aryl, heteroaryl
n = 0, 1

Scheme 5 shows the synthesis of compounds of the formula:

e.g., compounds of formula (IX), formula (X), and formula (XI).

Scheme 5

X = O, S
Y = CH, N
$Y^1$ = CH, N
Z = S, N, NH
$R^1$ = H, alkyl, cycloalkyl, aryl, heteroaryl
n = 0, 1

Scheme 6 shows the synthesis of compounds of the formula:

e.g., compounds of formula (XIV).

Scheme 6

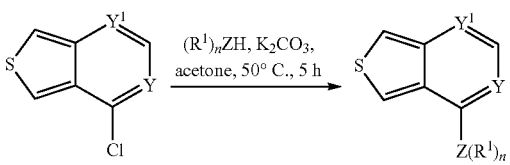

Y = CH, N
$Y^1$ = CH, N
Z = S, N, NH
$R^1$ = H, alkyl, cycloalkyl, aryl, heteroaryl
n = 0, 1

Example 2

Activators of Autophagic Flux and Phospholipase D

The WHYKD series of compounds were synthesized for optimal brain penetrance based on the molecular weight (MW) and partition coefficient (log P), according to Lipinski's Rule for CNS penetrance: MW≤400, log P≤5.

Activators according to the formula:
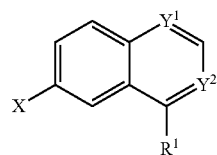
were synthesized according to the schemes above. Molecular weights and log P were calculated. Results are shown in Table 1 below.
TABLE 1
| STRUCTURE | PROJECT ID | M.W. | log P | X | $Y^1$ | $Y^2$ | $R^1$ |
|---|---|---|---|---|---|---|---|
| 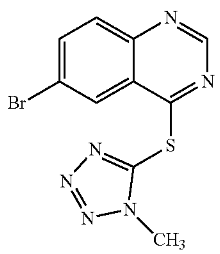 | WHYKD3 | 323.17 | 3.85 | Br | N | N | thioheteroaryl |
| 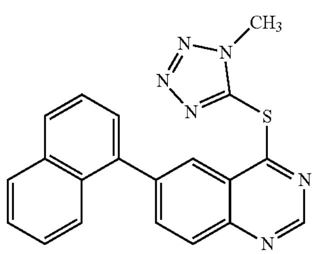 [SMILES: Cn1nnnc1Sc1ncnc2ccc(-c3cccc4ccccc34)cc12] | WHYKD4 | 369.44 | 5.69 | aryl | N | N | Thioheteroaryl |
| 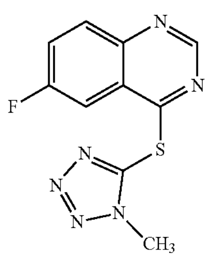 [SMILES: Cn1nnnc1Sc1ncnc2ccc(F)cc12] | WHYKD5 | 262.27 | 3.18 | F | N | N | Thioheteroaryl |
| 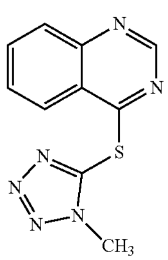 [SMILES: Cn1nnnc1Sc1ncnc2ccccc12] | WHYKD6 | 244.28 | 3.02 | H | N | N | thioheteroaryl |
| 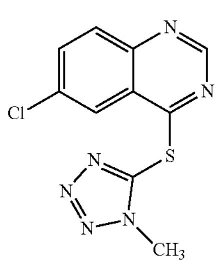 [SMILES: Cn1nnnc1Sc1ncnc2ccc(Cl)cc12] | WHYKD7 | 278.72 | 3.58 | Cl | N | N | thioheteroaryl |

TABLE 1-continued

| STRUCTURE | PROJECT ID | M.W. | log P | X | Y¹ | Y² | R¹ |
|---|---|---|---|---|---|---|---|
| 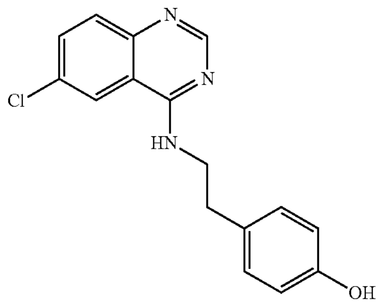 [SMILES: Oc1ccc(CCNc2ncnc3ccc(Cl)cc23)cc1] | WHYKD8 | 299.76 | 3.91 | Cl | N | N | (2-aminoethyl)aryl |
| 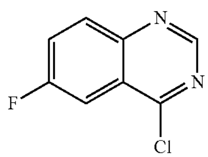 | WHYKD9 | 182.58 | 2.58 | F | N | N | Cl |
| 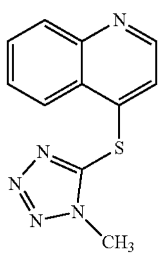 [SMILES: Cn1nnnc1Sc1ccnc2ccccc12] | WHYKD10 | 243.29 | 2.9 | H | N | CH | thioheteroaryl |
| 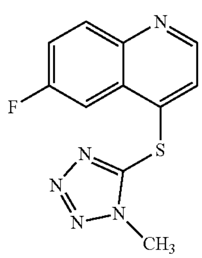 [SMILES: Cn1nnnc1Sc1ccnc2ccc(F)cc12] | WHYKD11 | 261.28 | 3.06 | F | N | CH | thioheteroaryl |
| 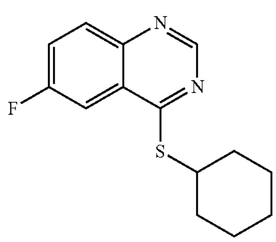 [SMILES: Fc1ccc2ncnc(SC3CCCCC3)c2c1] | WHYKD12 | 262.35 | 4.38 | F | N | N | thiocycloalkyl |
| 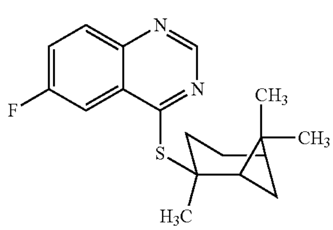 [SMILES: CC1(Sc2ncnc3ccc(F)cc23)CCC2CC1C2(C)C] | WHYKD13 | 316.44 | 5.21 | F | N | N | thiocycloalkyl |

TABLE 1-continued
| STRUCTURE | PROJECT ID | M.W. | log P | X | Y¹ | Y² | R¹ |
|---|---|---|---|---|---|---|---|
| 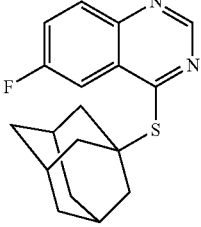 | WHYKD14 | 314.42 | 4.66 | F | N | N | thiocycloalkyl |
| 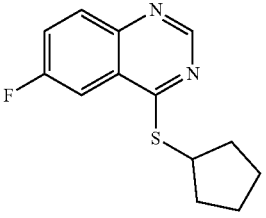 [SMILES: Fc1ccc2ncnc(SC3CCCC3)c2c1] | WHYKD15 | 248.32 | 3.96 | F | N | N | thiocycloalkyl |
| 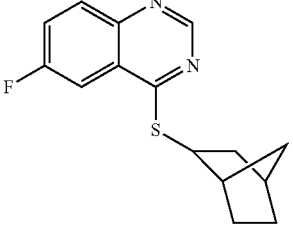 | WHYKD16 | 274.36 | 4.19 | F | N | N | thiocycloalkyl |
| 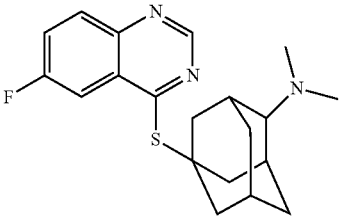 [SMILES: CN(C)C1C2CC3CC1CC(Sc1ncnc4ccc(F)cc14)(C3)C2] | WHYKD17 | 357.49 | 4.09 | F | N | N | thiocycloalkyl |
| 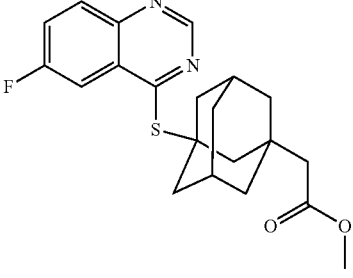 | WHYKD18 | 386.48 | 4.41 | F | N | N | thiocycloalkyl |
| 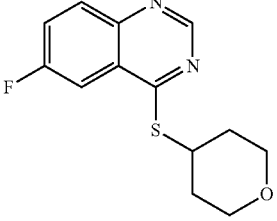 | WHYKD19 | 264.32 | 2.63 | F | N | N | thiocycloalkyl |

TABLE 1-continued
| STRUCTURE | PROJECT ID | M.W. | log P | X | $Y^1$ | $Y^2$ | $R^1$ |
|---|---|---|---|---|---|---|---|
| 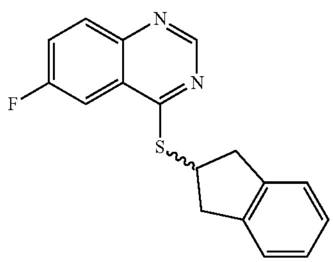 [SMILES: Fc1ccc2ncnc(SC3Cc4ccccc4C3)c2c1] | WHYKD20 | 296.36 | 4.8 | F | N | N | thoaryl |
| 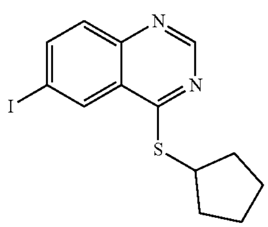 [SMILES: Ic1ccc2ncnc(SC3CCCC3)c2c1] | WHYKD30 | 356.23 | 5.16 | I | N | N | thiocycloalkyl |
Activators according to the formula:
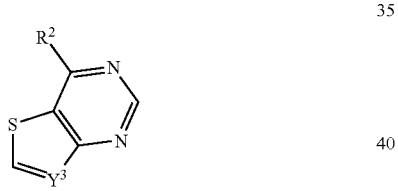
were synthesized according to the schemes above. Molecular weights and log P were calculated. Results are shown in Table 2 below.
TABLE 2
| STRUCTURE | PROJECT ID | M.W. | log P | $Y^3$ | $R^2$ |
|---|---|---|---|---|---|
| 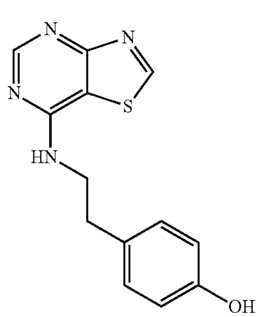 [SMILES: Oc1ccc(CCNc2ncnc3ncsc23)cc1] | WHYKD21 | 272.33 | 3.36 | N | (2-aminoethyl)aryl |
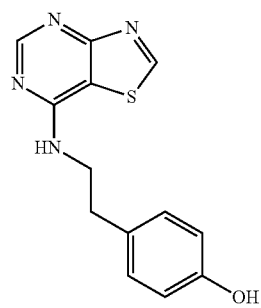

TABLE 2-continued
| STRUCTURE | PROJECT ID | M.W. | log P | $Y^3$ | $R^2$ |
|---|---|---|---|---|---|
| 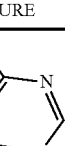 | WHYKD23 | 271.34 | 3.66 | CH | (2-aminoethyl)aryl |
Activators according to the formula:
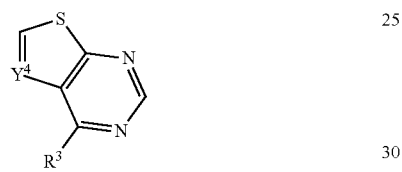 (25)
were synthesized according to the schemes above. Molecular weights and log P were calculated. Results are shown in Table 3 below.
TABLE 3
| STRUCTURE | PROJECT ID | M.W. | log P | $Y^4$ | $R^3$ |
|---|---|---|---|---|---|
| 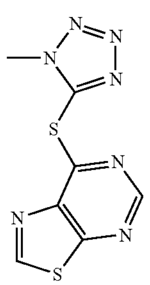 [SMILES: Cn1nnnc1Sc1ncnc2scnc12] | WHYKD1 | 251.29 | 2.56 | N | thioheteroaryl |
| 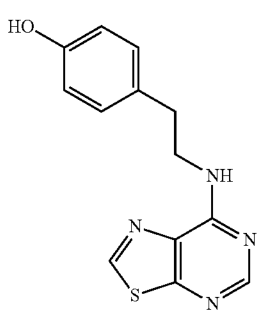 [SMILES: Oc1ccc(CCNc2ncnc3scnc23)cc1] | WHYKD2 | 272.33 | 2.89 | N | (2-aminoethyl)aryl |

TABLE 3-continued

| STRUCTURE | PROJECT ID | M.W. | log P | Y⁴ | R³ |
|---|---|---|---|---|---|
| (structure shown) | WHYKD22 | 271.34 | 3.34 | CH | (2-aminoethyl)aryl |

Activators according to the formula:

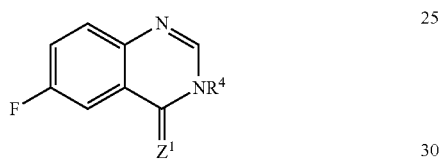

were synthesized according to the schemes above. Molecular weights and log P were calculated. Results are shown in Table 4 below.

TABLE 4

| STRUCTURE | PROJECT ID | M.W. | log P | X | Y¹ | Y² | R⁴ | Z¹ |
|---|---|---|---|---|---|---|---|---|
| (structure shown) | WHYKD24 | 164.14 | 1.02 | F | N | N | H | O |

Example 3

Design of Derivatives

Several series of derivatives were synthesized based on the following lead compounds:

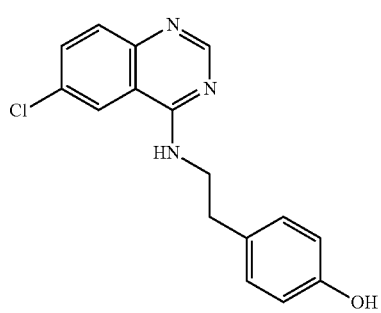

Original Lead

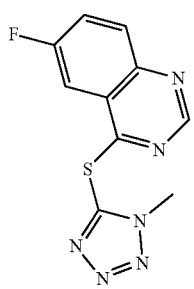

Additional Lead

In addition to log P, the topological polar surface area (tPSA), C Log P (log P calculated by group contribution method), and Log S (solubility) were calculated. Results are shown in the Tables below.

TABLE 5
Modifications to the core and side chain (Series 1)
| STRUCTURE | log P | tPSA | CLogP | LogS |
|---|---|---|---|---|
| 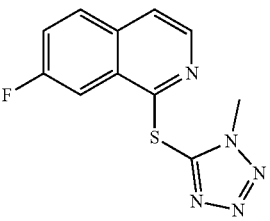 [SMILES: Cn1nnnc1Sc1nccc2ccc(F)cc12] | 3.35 | 52.68 | 2.65154 | −3.235 |
| 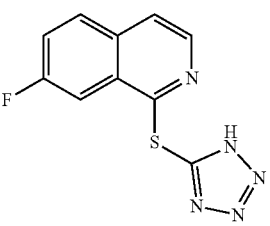 [SMILES: Fc1ccc2ccnc(Sc3nnn[nH]3)c2c1] | 3.12 | 61.47 | 2.34241 | −3.295 |
| 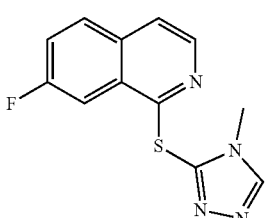 | 2.94 | 40.32 | 1.83259 | −4.663 |
| 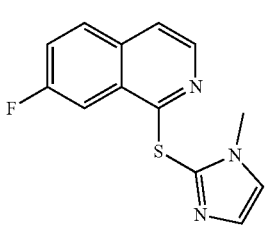 [SMILES: Cn1ccnc1Sc1nccc2ccc(F)cc12] | 3.19 | 27.96 | 3.25375 | −3.864 |
| 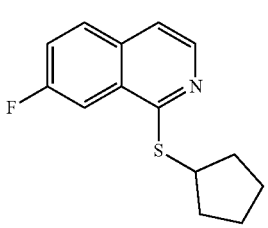 [SMILES: Fc1ccc2ccnc(SC3CCCC3)c2c1] | 4.14 | 12.36 | 4.64041 | −4.354 |
| 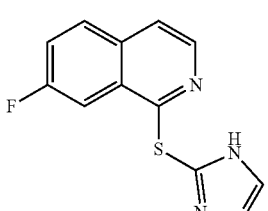 | 2.71 | 49.11 | 2.01759 | −4.354 |
| 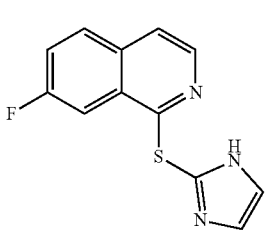 [SMILES: Fc1ccc2ccnc(Sc3ncc[nH]3)c2c1] | 2.95 | 36.75 | 3.23654 | −3.554 |

TABLE 5-continued
Modifications to the core and side chain (Series 1)
| STRUCTURE | log P | tPSA | CLogP | LogS |
|---|---|---|---|---|
| 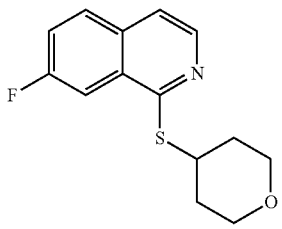 [SMILES: Fc1ccc2ccnc(SC3CCOCC3)c2c1] | 2.8 | 21.59 | 2.80041 | −3.813 |
| 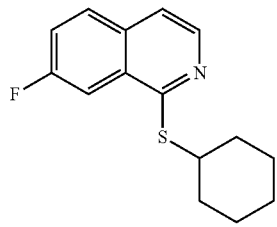 [SMILES: Fc1ccc2ccnc(SC3CCCCC3)c2c1] | 4.56 | 12.36 | 5.19941 | −4.832 |
TABLE 6
Modifications to the core and side chain (Series 2)
| STRUCTURE | log P | tPSA | CLogP | LogS |
|---|---|---|---|---|
| 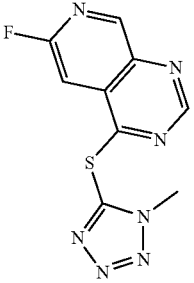 [SMILES: Cn1nnnc1Sc1ncnc2cnc(F)cc12] | 2.31 | 77.4 | 0.803829 | −1.704 |
| 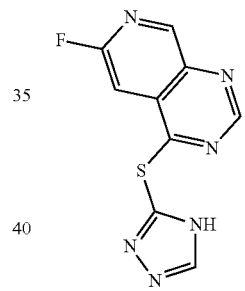 | 2.07 | 86.19 | 0.539011 | −1.765 |
| 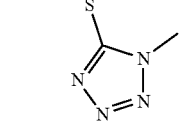 | 1.9 | 65.04 | −0.0366305 | −3.133 |
| 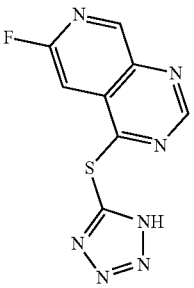 [SMILES: Fc1cc2c(Sc3nnn[nH]3)ncnc2cn1] | 1.66 | 7383 | 0.148224 | −2.824 |
| 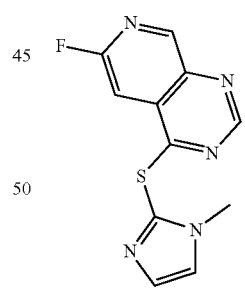 | 2.14 | 52.68 | 1.40054 | −2.334 |
| 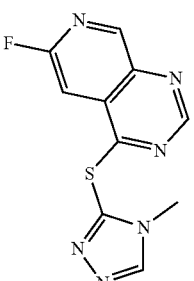 | 1.91 | 61.47 | 1.38428 | −2.024 |

TABLE 6-continued
Modifications to the core and side chain (Series 2)
| STRUCTURE | log P | tPSA | CLogP | LogS |
|---|---|---|---|---|
| 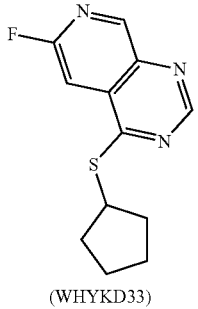 [SMILES: "(WHYKD33)" ; Fc1cc2c(SC3CCCC3)ncnc2cn1] (WHYKD33) | 3.09 | 37.08 | 2.83701 | −2.823 |
| 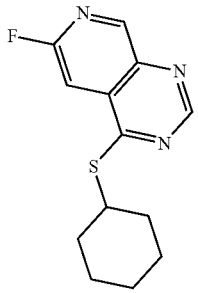 [SMILES: Fc1cc2c(SC3CCCCC3)ncnc2cn1] | 3.51 | 37.08 | 3.39601 | −3.301 |
| 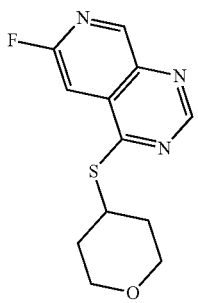 [SMILES: Fc1cc2c(SC3CCOCC3)ncnc2cn1] | 1.76 | 46.31 | 0.997011 | −2.283 |
TABLE 7
Modifications to the core and side chain (Series 3)
| STRUCTURE | log P | tPSA | CLogP | LogS |
|---|---|---|---|---|
| 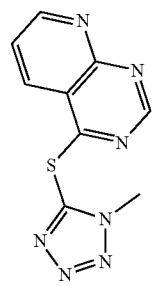 [SMILES: Cn1nnnc1Sc1ncnc2ncccc12] | 2.89 | 77.4 | 0.647513 | −1.626 |
| 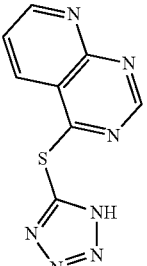 | 2.65 | 86.19 | 0.382662 | −1.686 |
| 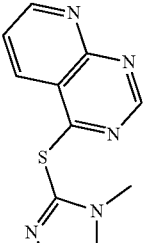 | 2.48 | 65.04 | −0.192932 | −3.117 |
| 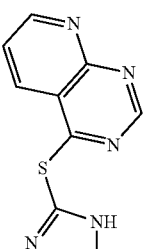 | 2.25 | 73.83 | −0.00808129 | −2.806 |
| 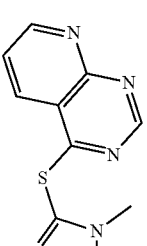 | 2.73 | 52.68 | 1.24423 | −2.303 |
| 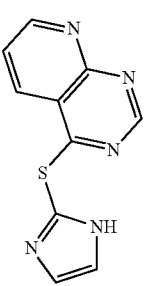 [SMILES: c1cnc2ncnc(Sc3ncc[nH]3)c2c1] | 2.49 | 61.47 | 1.22796 | −1.992 |

TABLE 7-continued

Modifications to the core and side chain (Series 3)

| STRUCTURE | log P | tPSA | CLogP | LogS |
| --- | --- | --- | --- | --- |
| (WHYKD35) | 3.68 | 37.08 | 2.68066 | −2.893 |
| 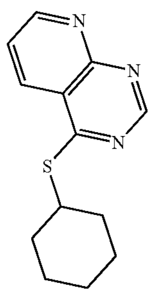 [SMILES: c1cnc2ncnc(SC3CCCCC3)c2c1] | 4.09 | 37.08 | 3.23966 | −3.372 |
| 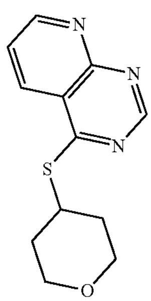 [SMILES: c1cnc2ncnc(SC3CCOCC3)c2c1] | 2.34 | 46.31 | 0.840662 | −2.256 |

TABLE 8

Modifications to the core and side chain (Series 4)

| STRUCTURE | log P | tPSA | CLogP | LogS |
| --- | --- | --- | --- | --- |
| 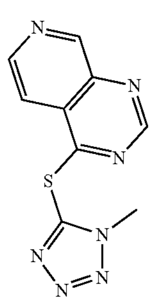 [SMILES: Cn1nnnc1Sc1ncnc2cnccc12] | 1.68 | 77.4 | 0.647513 | −1.441 |

TABLE 8-continued

Modifications to the core and side chain (Series 4)

| STRUCTURE | log P | tPSA | CLogP | LogS |
| --- | --- | --- | --- | --- |
| 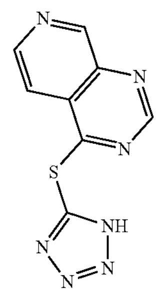 [SMILES: c1cc2c(Sc3nnn[nH]3)ncnc2cn1] | 1.45 | 86.19 | 0.382662 | −1.501 |
|  | 1.28 | 65.04 | −0.192932 | −2.932 |
| 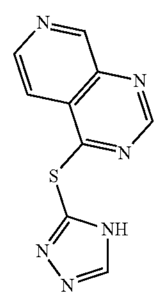 [SMILES: c1cc2c(Sc3nnc[nH]3)ncnc2cn1] | 1.04 | 73.83 | −0.0080129 | −2.621 |
| 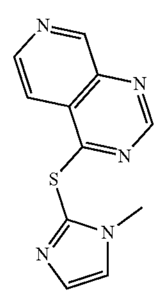 [SMILES: Cn1ccnc1Sc1ncnc2cnccc12] | 1.52 | 52.68 | 1.24423 | −2.119 |
|  | 1.28 | 61.47 | 1.22796 | −1.808 |

TABLE 8-continued
Modifications to the core and side chain (Series 4)
| STRUCTURE | log P | tPSA | CLogP | LogS |
|---|---|---|---|---|
| 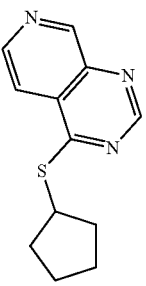 [SMILES: c1cc2c(SC3CCCC3)ncnc2cn1] | 2.47 | 37.08 | 2.68066 | −2.704 |
| 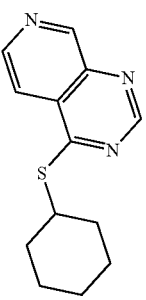 [SMILES: c1cc2c(SC3CCCCC3)ncnc2cn1] | 2.89 | 37.08 | 3.23966 | −3.183 |
| 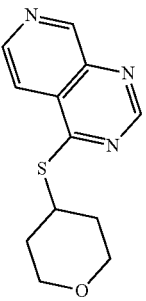 [SMILES: c1cc2c(SC3CCOCC3)ncnc2cn1] | 1.13 | 46.31 | 0.840662 | −2.071 |
TABLE 9
Modifications to the core and side chain (Series 5)
| STRUCTURE | log P | tPSA | CLogP | LogS |
|---|---|---|---|---|
| 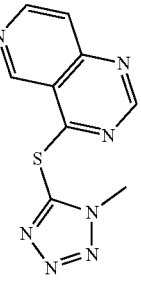 | 1.68 | 77.4 | 0.647513 | −1.466 |
TABLE 9-continued
Modifications to the core and side chain (Series 5)
| STRUCTURE | log P | tPSA | CLogP | LogS |
|---|---|---|---|---|
| 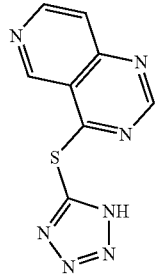 [SMILES: c1cc2ncnc(Sc3nnn[nH]3)c2cn1] | 1.45 | 86.19 | 0.382662 | −1.526 |
| 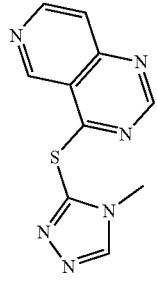 [SMILES: Cn1cnnc1Sc1ncnc2ccncc12] | 1.28 | 65.04 | −0.192932 | −2.957 |
| 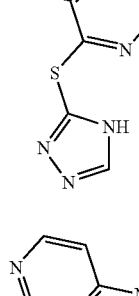 | 1.04 | 73.83 | −0.00808129 | −2.646 |
| 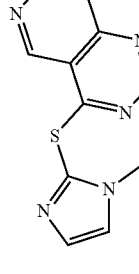 | 1.52 | 52.68 | 1.24423 | −2.144 |
| 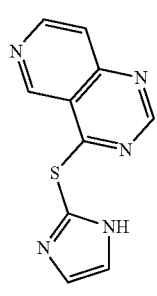 [SMILES: c1cc2ncnc(Sc3ncc[nH]3)c2cn1] | 1.28 | 61.47 | 1.22796 | −1.832 |

TABLE 9-continued
Modifications to the core and side chain (Series 5)
| STRUCTURE | log P | tPSA | CLogP | LogS |
|---|---|---|---|---|
| 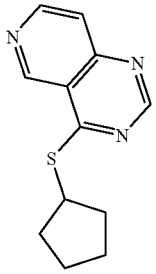 [SMILES: c1cc2ncnc(SC3CCCC3)c2cn1] | 2.47 | 37.08 | 3.23966 | −2.733 |
| 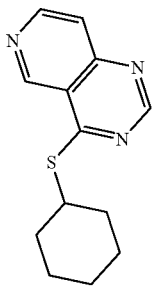 [SMILES: c1cc2ncnc(SC3CCCCC3)c2cn1] | 2.89 | 37.08 | 3.23966 | −3.212 |
| 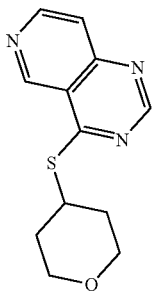 [SMILES: c1cc2ncnc(SC3CCOCC3)c2cn1] | 1.13 | 46.31 | 0.840662 | −2.096 |
TABLE 10
Modifications to the core and side chain (Series 6)
| STRUCTURE | log P | tPSA | CLogP | LogS |
|---|---|---|---|---|
| 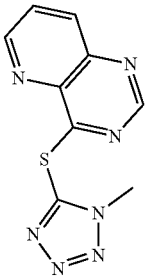 [SMILES: Cn1nnnc1Sc1ncnc2cccnc12] | 2.11 | 77.4 | 0.857513 | −1.525 |
TABLE 10-continued
Modifications to the core and side chain (Series 6)
| STRUCTURE | log P | tPSA | CLogP | LogS |
|---|---|---|---|---|
| 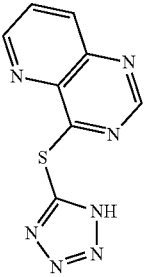 [SMILES: c1cnc2c(Sc3nnn[nH]3)ncnc2c1] | 1.87 | 86.19 | 0.592663 | −1.585 |
| 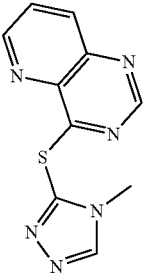 [SMILES: Cn1cnnc1Sc1ncnc2cccnc12] | 1.7 | 65.04 | 0.0170677 | −3.017 |
| 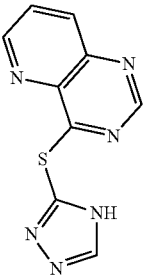 [SMILES: c1cnc2c(Sc3nnc[nH]3)ncnc2c1] | 1.46 | 73.83 | 0.201919 | −2.705 |
| 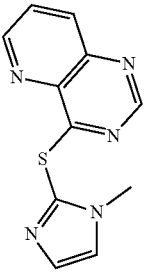 [SMILES: Cn1ccnc1Sc1ncnc2cccnc12] | 1.94 | 52.68 | 1.45423 | −2.203 |
| 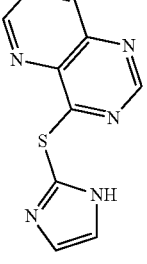 | 1.71 | 61.47 | 1.43796 | −1.892 |

TABLE 10-continued
Modifications to the core and side chain (Series 6)
| STRUCTURE | log P | tPSA | CLogP | LogS |
|---|---|---|---|---|
| 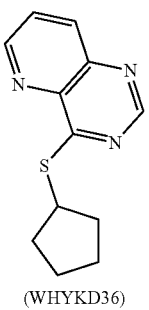 (WHYKD36) | 2.89 | 37.08 | 2.89066 | −2.787 |
| 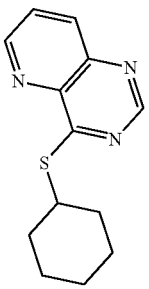 [SMILES: c1cnc2c(SC3CCCCC3)ncnc2c1] | 3.31 | 37.08 | 3.44966 | −3.266 |
| 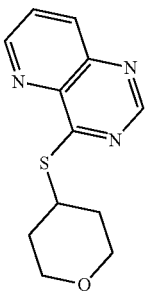 [SMILES: c1cnc2c(SC3CCOCC3)ncnc2c1] | 1.55 | 46.31 | 1.05066 | −2.155 |
TABLE 11
Modifications to the core and side chain (Series 7)
| STRUCTURE | log P | tPSA | CLogP | LogS |
|---|---|---|---|---|
| 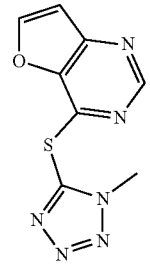 [SMILES: Cn1nnnc1Sc1ncnc2ccoc12] | 1.63 | 74.27 | 1.1098 | −1.275 |
| 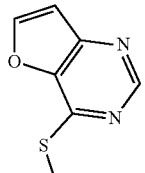 | 1.4 | 83.06 | 0.834 | −1.333 |
| 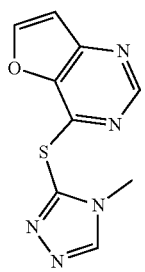 [SMILES: Cn1cnnc1Sc1ncnc2ccoc12] | 1.23 | 61.91 | 0.272969 | −2.704 |
| 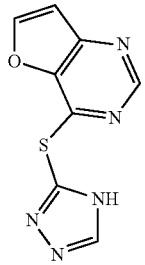 [SMILES: c1nc(Sc2nnc[nH]2)c2occc2n1] | 0.99 | 70.7 | 0.457768 | −2.391 |
| 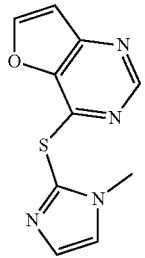 [SMILES: Cn1ccnc1Sc1ncnc2ccoc12] | 1.47 | 49.55 | 1.70682 | −1.904 |
| 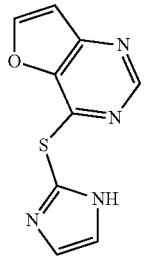 [SMILES: c1c[nH]c(Sc2ncnc3ccoc23)n1] | 1.24 | 58.34 | 1.69005 | −1.592 |

TABLE 11-continued
Modifications to the core and side chain (Series 7)
| STRUCTURE | log P | tPSA | CLogP | LogS |
|---|---|---|---|---|
| 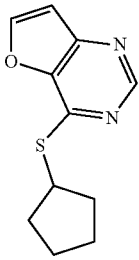 [SMILES: c1nc(SC2CCCC2)c2occc2n1] | 2.42 | 33.95 | 3.132 | −2.403 |
| 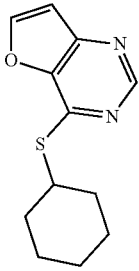 [SMILES: c1nc(SC2CCCCC2)c2occc2n1] | 2.84 | 33.95 | 3.691 | −2.883 |
| 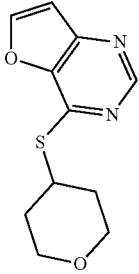 [SMILES: c1nc(SC2CCOCC2)c2occc2n1] | 1.08 | 43.18 | 1.292 | −1.864 |
TABLE 12
Modifications to the core and side chain (Series 8)
| STRUCTURE | log P | tPSA | CLogP | LogS |
|---|---|---|---|---|
| 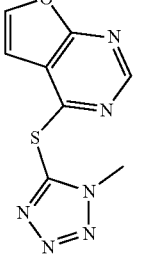 | 1.96 | 74.27 | 0.8996 | −1.745 |
| 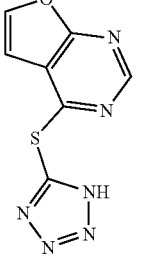 | 1.72 | 83.06 | 0.624 | −1.803 |
TABLE 12-continued
Modifications to the core and side chain (Series 8)
| STRUCTURE | log P | tPSA | CLogP | LogS |
|---|---|---|---|---|
| 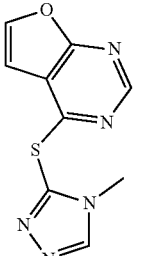 | 1.55 | 61.91 | 0.0629689 | −3.174 |
| 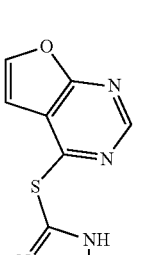 | 1.31 | 70.7 | 0.247768 | −2.862 |
| 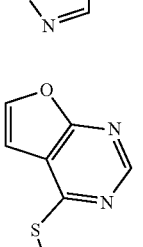 | 1.79 | 49.55 | 1.49682 | −2.374 |
| 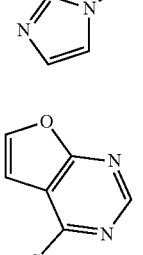 | 1.56 | 58.34 | 1.48005 | −2.062 |
| 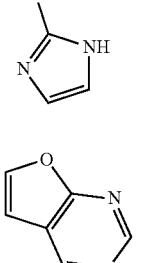 | 2.74 | 33.95 | 2.922 | −2.874 |

TABLE 12-continued
Modifications to the core and side chain (Series 8)
| STRUCTURE | log P | tPSA | CLogP | LogS |
|---|---|---|---|---|
| 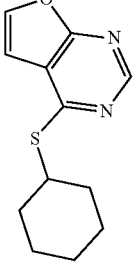 | 3.16 | 33.95 | 3.48 | −3.353 |
| 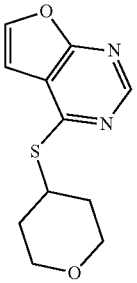 [SMILES: c1nc(SC2CCOCC2)c2ccoc2n1] | 1.4 | 43.18 | 1.082 | −2.335 |
TABLE 13
Modifications to the core and side chain (Series 9)
| STRUCTURE | log P | tPSA | CLogP | LogS |
|---|---|---|---|---|
| 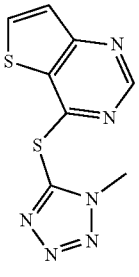 [SMILES: Cn1nnnc1Sc1ncnc2ccsc12] | 3.0 | 65.04 | 1.74907 | −2.051 |
| 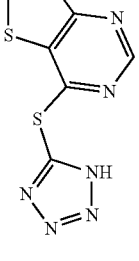 | 2.76 | 73.83 | 1.47586 | −2.109 |
| 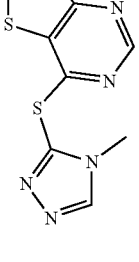 | 2.59 | 52.68 | 0.911314 | −3.542 |
TABLE 13-continued
Modifications to the core and side chain (Series 9)
| STRUCTURE | log P | tPSA | CLogP | LogS |
|---|---|---|---|---|
| 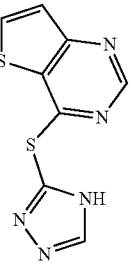 | 2.36 | 61.47 | 1.09641 | −3.23 |
| 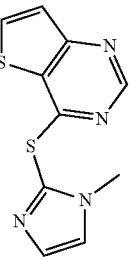 | 2.84 | 40.32 | 2.34546 | −2.728 |
| 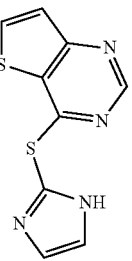 | 2.6 | 49.11 | 2.32952 | −2.416 |
| 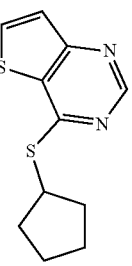 | 3.79 | 24.72 | 3.77388 | −3.323 |
| (WHYKD32) | | | | |
| 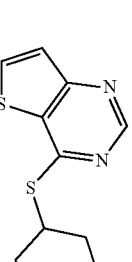 | 4.2 | 24.72 | 4.33286 | −3.802 |

TABLE 13-continued

Modifications to the core and side chain (Series 9)

| STRUCTURE | log P | tPSA | CLogP | LogS |
|---|---|---|---|---|
| 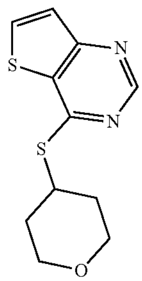 [SMILES: c1nc(SC2CCOCC2)c2sccc2n1] | 2.45 | 33.95 | 1.93386 | −2.687 |

TABLE 14

Modifications to the core and side chain (Series 10)

| STRUCTURE | log P | tPSA | CLogP | LogS |
|---|---|---|---|---|
| 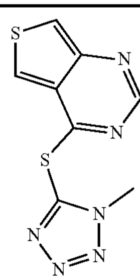 | 2.94 | 65.04 | 1.53907 | −2.188 |
| 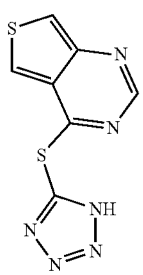 [SMILES: c1nc(Sc2nnn[nH]2)c2cscc2n1] | 2.71 | 73.83 | 1.26586 | −2.247 |
| 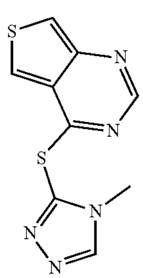 [SMILES: Cn1cnnc1Sc1ncnc2cscc12] | 2.54 | 52.68 | 0.701314 | −3.68 |
| 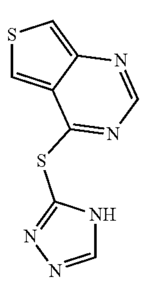 [SMILES: c1nc(Sc2nnc[nH]2)c2cscc2n1] | 2.3 | 61.47 | 0.886405 | −3.367 |

TABLE 14-continued

Modifications to the core and side chain (Series 10)

| STRUCTURE | log P | tPSA | CLogP | LogS |
|---|---|---|---|---|
| 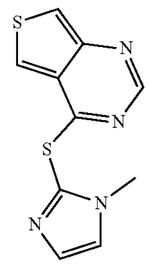 [SMILES: Cn1ccnc1Sc1ncnc2cscc12] | 2.78 | 40.32 | 2.13546 | −2.866 |
| 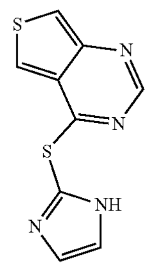 [SMILES: c1c[nH]c(Sc2ncnc3cscc23)n1] | 2.55 | 49.11 | 2.11952 | −2.554 |
| 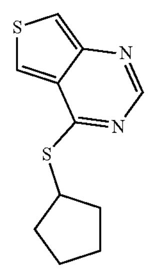 [SMILES: c1nc(SC2CCCC2)c2cscc2n1] | 3.73 | 24.72 | 3.56386 | −3.468 |
| 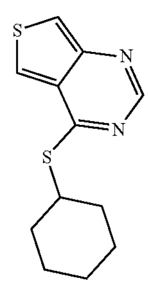 [SMILES: c1nc(SC2CCCCC2)c2cscc2n1] | 4.15 | 24.72 | 4.12286 | −3.947 |
| 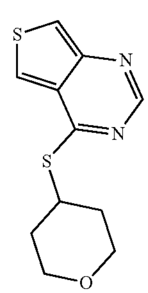 [SMILES: c1nc(SC2CCOCC2)c2cscc2n1] | 2.39 | 33.95 | 1.72386 | −2.824 |

TABLE 15

Quinazolinones (Series 11)

| STRUCTURE | log P | tPSA | CLogP | LogS |
|---|---|---|---|---|
| 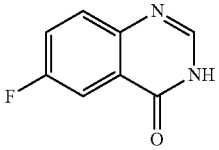 | 1.02 | 41.46 | 0.506065 | −1.702 |
| 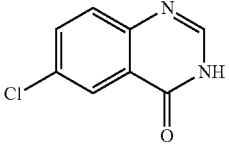 | 1.42 | 41.46 | 1.07606 | −2.152 |
| 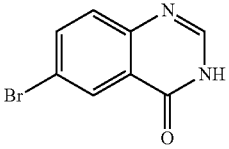 [SMILES: O=c1[nH]cnc2ccc(Cl)cc12] | 1.69 | 41.46 | 1.22606 | −2.273 |
| 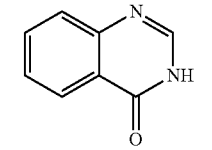 [SMILES: O=c1[nH]cnc2ccccc12] | 0.86 | 41.46 | 0.305 | −1.452 |

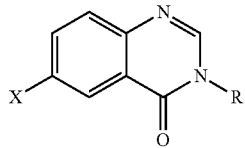

X = F, Cl, Br, H

R = H, CH$_3$, Et, CF$_3$, 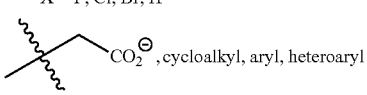CO$_2^\ominus$, cycloalkyl, aryl, heteroaryl Example 4

Biological Testing of WHYKD Compounds

The assays listed below were carried out using a transfected HEK 293 (Human Embryo Kidney) cell line that has been engineered to express fluorescently tagged (mKate2) Tau (unless otherwise noted). The cells were grown in the presence of the antibiotic doxycycline. When the antibiotic is removed the cells produce Tau (which can be quantified), thus allowing the test compounds' effects on Tau's production to be compared. Doxycycline was removed for 72 hours prior to exposure to the test compounds to promote sufficient Tau production. Cells were subsequently plated into plates for each of the assays described below.

Autophagy, Aggregate and Tau-mKate2 IC50 Assays

Preparation of Plated Tet-Regulated HEK 293 Cells (Jump-In™ Cells)

1) HEK cells with tet-regulated expression of mKate2 tagged Tau were grown in DMEM medium (Dulbecco's Modified Eagle's Medium) containing 0.5 µg/mL doxycycline (Dox)(MP-Bio #198955), after 3-5 days Dox was removed by washing the cells twice with sterile phosphate buffered saline (PBS; Invitrogen #14190-144), cells were left in DMEM without Dox for 72 hours (to further clear remaining Dox in cells).

2) 96 well, black plates with ultra-thin clear bottom (Costar #3720) were coated with Poly D Lysine (PDL) (Sigma-p0899-M wt. 70,000-150,000) or commercially sourced transparent polystyrene/glass bottom plates were used and coated. PDL was aspirated after 2 hours and plates were allowed to dry out for another 2-3 hours. The coating procedure was completed under sterile conditions. Plates were used immediately after coating.

3) Cells were detached from the flasks using triple express (Invitrogen #12605-010) and plated in PDL-coated 96 well plates. For plating, 200 µL of medium was added to each well at a concentration of 400 k cells/ml (80 k cells/well). 1 row of peripheral wells on all sides was spared to prevent any changes in experimental conditions due to evaporation from these wells. Warm medium/PBS (containing no cells) was pipetted into the peripheral wells and PBS was pipetted into spaces between wells to maintain homogenous conditions across the central wells. Cells were then allowed to settle down and attach to the bottom of the plate for 18-24 hours.

Treatment and Staining with Cyto-ID™

Cyto-ID™ assay measures autophagic vacuoles and monitors autophagic flux in lysosomally inhibited live cells using a novel dye that selectively labels accumulated autophagic vacuoles. The dye used in the kit prevents its accumulation within lysosomes, but enables labelling of vacuoles associated with the autophagy pathway using the LC3 biomarker.

The test compounds (along with CytoID™ dye and Hoechst stain) were added to the cells and incubated for 3 hours. Reference compounds were also used in each plate, Rapamycin was used for autophagy induction and chloroquine was used for lysosomal inhibition. After 3 hours test compound was aspirated off and kept. Cells were then washed and read using a fluorescence plate reader. Hoescht, Cyto-ID™ and mKate2 were measured using 3 distinct wavelengths on the plate reader. The Hoescht measurement allowed normalisation of results across wells. After reading, test compound was re-added and the cells are left for a further 21 hours. At the 24 hour time point cells were once again washed and plates read using the fluorescence plate reader.

1) Before initiating treatment, all wells were washed once with warm FluoroBrite™ (FB) DMEM (Dulbecco's Modified Eagle's Medium) (Invitrogen # A18967-01) with 10% Fetal Bovine Serum, dialyzed (FBS; Invitrogen #26400-044) and 1% MEM (Minimal Essential Media) NEAR (Non Essential Amino Acids). 280 µl of warm medium/PBS was maintained in peripheral wells.

2) Test samples were prepared in warm FluoroBrite™ DMEM and with 10% FBS and 1% NEAA (FB-DMEM). Rapamycin 200 nM (Enzo # BML-A275-0025) was used for autophagy induction and 15 mM chloroquine was used for lysosomal inhibition (bafilomycin or similar compounds were not used as they give a false negative result in the assay). Dimethyl Sulfoxide 1:1000 (DMSO; Fisher # BP231-100) was used as control. Autophagosome marker Cyto ID™ (1:500; Enzo # ENZ-51031-k200) and Hoechst (1:200) was added to these test sample preparations before treating the cells.

3) The treatment groups were staggered in order to obtain similar conditions across all groups. For an n=6, 3 control wells were near the periphery and 3 were near the center of the plate, same was true for Rapamycin and any other drug treatments.

4) Cells were treated/stained for 3 hours at 37° C. At 3 hours post-treatment, test sample preparation containing Cyto-ID™ was carefully aspirated and transferred to a fresh sterile microplate (Falcon #353072) for reuse. Medium in the treatment plate was immediately replaced with warm FB-DMEM. The new plate with test compound preparations was placed in an incubator at 37° C.

5) Treatment plate was then washed quickly 3 times with warm FB-DMEM (100 µL/well). After the 3rd wash 50 µL of warm medium was left in each well. At this point, the plate was ready for reading. See details in Reading Plate section. Hoescht was read at Excitation wavelength (Ex) =355 nm & Emission wavelength (Em)=446 nm. mKate2 was read at Ex=575 nm & Em=630 nm. Cyto-ID™ was read at Ex=463 nm & Em=534 nm.

6) Afterwards, medium was replaced with corresponding wells of the plate containing test compound/stain preparation and re-incubated at 37° C.

7) At 24 hours post reaction all medium was aspirated and the plate was washed 3 times with warm FB-DMEM, and read again for Hoescht (Ex=355 nm Em=446 nm), CytoID™ (Ex=463 nm; Em=534 nm) and mKate2 (Ex=575 nm; Em=630 nm) in 80 µl of FB-DMEM.

Proteostat™ Protein Aggregation Assay

Proteostat™ assay was used to detect aggresomes via measurement of p62. Aggresomes are inclusion bodies that form when the ubiquitin-proteasome machinery is overwhelmed with aggregation-prone proteins. Typically, an aggresome forms in response to some cellular stress, such as hyperthermia, viral infection, or exposure to reactive oxygen species. Aggresomes may provide a cytoprotective function by sequestering the toxic, aggregated proteins and may also facilitate their ultimate elimination from cells by autophagy. Following the final plate read described in the Cyto-ID™ assay described above, Proteostat™ detection reagent was added to every well and the plate was incubated for 15 minutes. Following this incubation, the plate was read by fluorescence plate reader at the specified wavelength. After this plate read, the cells were fixed by incubating with warm paraformaldehyde for 8 minutes. The fixed cells were then read by plate reader as before.

8) Detection solution was prepared by adding 10 µl Proteostat™ detection reagent (ENZ-51023-KP002) and 200 µL of 10× assay buffer into 1790 µL water and mixing well.

9) 20 µL was added per well (each well had 80 µl of Fluorobrite™ media with no FBS) and incubated in the dark for 15 min at room temperature.

10) Fluorescence for Proteostat™ (Ex=550 nm; Em=600 nm) was then read.

11) Plate was fixed by adding warm 4% paraformaldehyde 100 µL (PFA; EMS #15710) to all the wells and was incubated at room temperature for 8 min. PFA was removed and plate was washed with PBS (room temp) 3 times.

12) Plate was read again with fixed cells and same configuration at plate reader.

Note: CytoID™ and Proteostat™ are measures for LC3 and p62, which can be substituted using fluorescent tagged antibodies with corresponding fluorophores.

Reading Plate using Tecan M200

13) Plate was transferred to plate reader (Tecan Infinite M200) and read at optimal gain for mKate2, Cyto ID™ and Proteostat™ (last read only).

14) Each well was read at 5 consistent locations per well for the three signals. Each of these 5 locations was flashed 25 times. Signal from each well was first recorded as an average of 25 flashes, and the final value was based on average of 5 read locations per well. A peripheral border of 1000 µm was spared in all wells to mitigate any inconsistencies in reads due to minor cell loss across the periphery resulting from aspiration and washings. Peripheral wells were used to detect any background noise due to medium or PBS.

15) mKate2 was read at Ex=575 nm and Em=630 nm. CytoID™ was read at Ex=463 nm and Em=534 nm. For the final read, Proteostat™ was read at Ex=490 nm and Em=600 nm. Excitation & Emission Bandwidth for all three reads were 9 nm & 20 nm respectively.

16) Calculations were initially subtracted from well background (media only well) and normalized using Hoescht levels, Reading Plate Using IN Cell Analyzer 2000 (High Content Imaging), 17) Plate was transferred to IN Cell analyzer 2000 and imaged for mKate2, Cyto ID™, Proteostat™ and Hoechst (last read only).

18) Each well was imaged at 4 consistent fields located around the center of the well. All images were taken using 20× objective. The average reading from these 4 fields was recorded as the reading for that corresponding well. No images were taken from periphery of the wells to mitigate any inconsistencies in reads due to minor cell loss across the periphery resulting from aspiration and washings. Peripheral wells were used to detect any background noise due to medium or PBS.

19) FITC/FITC filter (Ex=490 nm–bandwidth 20 nm/Em=525 nm–bandwidth 36 nm) was used to image Cyto ID™, mKate2 was imaged using TexasRed/TexasRed filters (Ex=579 nm–bandwidth 34 nm/Em=624 nm–bandwidth 40 nm). For the Proteostat™ images FITC/dsRed combination was used (Ex=490 nm–bandwidth 20 nm Em=605 nm–bandwidth 52 nm). Nuclei were imaged using DAPI/DAPI filter set (Ex=350 nm–bandwidth 50 nm/Em=455 nm–bandwidth 50 nm).

p62 Aggregate and Tau Aggregate Western Blot Assay

Western blot assays were performed to determine protein changes in Tau and p62. Cells were cultured as above and incubated with test compounds for 24 h. Following test compound incubation, the test compound was aspirated off and cells were washed before harvesting. Cells were spun at a low speed and supernatant was aspirated to leave the cell pellet. The cell pellet was then homogenized in buffer, centrifuged at high speed, and the supernatant aspirated and further separated into total fraction and aggregate fraction allowing quantification of soluble and insoluble proteins. Western blots were run on the samples, gels transferred to nitrocellulose and incubated with antibodies for Tau and p62. After incubation with secondary antibodies for detection, the bands of protein were quantified by chemiluminescence.

1) Jump-In™ cells (see above) were maintained in 0.5 µg/mL doxycycline until use.

2) Three days prior to plating, cells were replated at 40% confluency in media without doxycycline.

3) The day prior to experimentation, 750 000 cells were plated per well n a 6-well plate (250 000 cells in 12 well plate).

4) On the day of experiment, cells were washed in warmed HBSS (Hank's Balanced Salt Solution) twice before media containing test compound (n=3 per compound per dose) or vehicle were added to the wells (1.5 mL in 6 well, 600 µL in 12 well). Plates were incubated for 24 hours at 37° C. with 5% $CO_2$.

5) Cells were rinsed twice in warmed HBSS before harvesting in 1 mL HBSS and transferred to 1.5 mL microtubes 6) Samples were spun at 500×g for 2 min at 4° C., and HBSS supernatant aspirated, leaving only the cell pellet. The cell pellet may be flash frozen and stored at −80° C. until use.

Sample Preparation

7) The cell pellet was homogenized in RIPA+ (Radio-Immunoprecipitation Assay) buffer containing protease inhibitors and phosphatase inhibitors and gently homogenized using a cell homogenizer.

8) Samples were then centrifuged for 20 min at 20,000 g at 4° C.

9) The supernatant was transferred to a new tube.

10) The supernatant was quantified for protein concentration using the Pierce™ Protein Assay.

11) Total fraction: 200 µg of supernatant was used to make a 1 mg/ml protein solution by adding RIPA+ buffer to bring the volume to 130 µL and adding 20 µL of 1M DTT (dithiothreitol) (to make a final concentration of 100 mM DTT) and 50 µL of 4× Invitrogen NuPAGE LDS (lithium dodecyl sulfate) loading buffer (4×, 10 ml—NP0007) with 100 mM DTT.

12) Aggregate fraction: For aggregates, 100 µg of sample was brought up to a final volume of 900 µL.

13) 100 µL of 10% sarkosyl solution was added to the sample and rotated at 4° C. for 60 min.

14) The sample was then centrifuged at 100.000 g for 60 min at 4° C.

15) The supernatant was carefully removed, leaving the pellet undisturbed. The tube was inverted to remove any additional liquid. If there was excess liquid, steps 12-14 were repeated to ensure a pure aggregate sample. Pellets were resuspended and solubilized in 65 µL of PBS before the addition of 10 µL of 1M and 25 µL of 4× Invitrogen NuPAGE LDS loading buffer with 100 mM OTT.

Electrophoresis/Western Blot

16) Prior to loading, the samples were heated at 90° C. for 2 min. A quick spin of the samples was performed to ensure there was no condensation on the tube. The 4-12% Tris-Bis gel was prepared using 1×MOPS buffer (Invitrogen—NP0001) and anti-oxidant (NP0005). For the soluble fraction, 2 µg of sample was loaded to each well; for the insoluble fraction, 5 µg of sample was loaded per well. 8 µL of Invitrogen Sharp MW standard was then loaded (optimally, all wells had the same volume of sample buffer.)

17) Sample was electrophoresed at 150V for approximately 1 h 15 min (until the running dye reached the base of the gel.)

18) The gel was then equilibrated in transfer buffer (25 mM Tris-HCl pH 8.3, 192 mM glycine, 20% (v:v) methanol) for 5 min.

19) The gel was then removed and transferred onto 0.2 µM nitrocellulose (GE BA83 10600001) at 200 mA for 90 minutes.

20) After transfer, the blot was briefly stained (15 s) with 0.1% Ponceau S in 5% acetic acid to ensure consistent sample loading between lanes.

21) The blot was then rinsed in TBS-T (Tris-buffered saline-polysorbate) for 2 min to remove the Ponceau S stain prior to immunoprobing.

Immunodetection

22) Samples were blocked in 5% milk in TBST for 30 min, and then rinsed in TBS-T until all buffer was clear (no milk residues remained in solution).

23) Blots were incubated in primary antibody (1:4000 PHF1 or CP27 for tau; 1:4000 p62 Abnova for p62; 1:5000 GAPDH (glyceraldehyde 3-phosphate dehydrogenase) for loading control) overnight in SuperBlock™ TBS-T at 4° C. on a rocking table.

24) After primary antibody exposure, blots were washed three times in TBS-T for 15 min, 25) Blots were then incubated in 1:4000 secondary antibody (Jackson Laboratories goat anti-mouse HRP conjugate).

26) After secondary, blots were washed three times in TBST for 15 min.

27) Blots were then developed using Millipore chemiluminescent fluid (1 ml per reagent; WBKLS0500) and detected using a Fuji LAS3000 Imaging unit at increments of 10 seconds.

28) Images were quantified using resident software or NIH Image J.

PLD Assay

Cells were incubated with test compound for 24 hours. 25 minutes prior to harvest at 24 hours, 3% ethanol solution was added to the wells to catalyze cleavage of the phospholipid. Cells were then placed on ice, washed and harvested. The harvested cells were centrifuged and the supernatant was aspirated and the pellet kept. The pellet was resuspended and chloroform/methanol lipid extraction was performed. The sample was centrifuged and the organic layer was separated, dried under nitrogen and stored at −80° C. On the day of analysis, samples were resuspended and analysed by LC/MS. All phosphatidylethanol species (PEtOH32-40: 0-6:16/18:0/1) were combined together and represented as total lipid content (all lipid species).

The assay was run in e18 primary cortical neurons from PLD1 or PLD2 KO mice cultured for 14 days. Alternatively, the assay can be run in the cells described above in the presence of excess PLD1 or PLD2 inhibitor to preclude that particular action from contributing to the effect of the drug.

1) Jump-In™ cells (see above) were maintained in 0.5 µg/mL doxycycline until use. For neurons, e18 fetuses were used, cortical neurons extracted and plated onto PLD-collagen coated 6 well plates and incubated for 14 days prior to use.

2) Three days prior to plating, cells were replated at 40% confluency in media without doxycycline.

3) The day prior to experimentation, 750 000 cells were plated per well in a 6-well plate (250 000 cells in 12 well plate).

4) On the day of experiment, cells were washed in warmed HBSS twice before media containing test compound (n=3 per compound per dose), inhibitor (355 nM ML298 or 50 nM VU0150669), or vehicle are added to the wells (1.5 mL in 6 well, 600 µL in 12 well). Plates were incubated for 24 hours at 37° C. with 5% $CO_2$.

5) 25 minutes prior to harvest, a 165 µL of a 3% ethanol solution was added to each well.

6) For harvesting, plates were placed on ice and cells were rinsed twice with ice cold HBSS before harvesting in 1 mL HBSS and transferring to 1.5 mL microtubes.

7) Samples were spun at 500×g for 2 min at 4° C., and HBSS supernatant aspirated, leaving only the cell pellet. The cell pellet could be flash frozen and stored at −80° C. until use.

TABLE 17

Biological Testing of WHKD Compounds 30-36

| Compound | LC50 (mM) | EC50 (nM) - Proteostat | EC50 (nM) - mKate2 | TI - mKate2 |
|---|---|---|---|---|
| WHYKD30 | >200 | 2510 | 1113 | 180 |
| WHYKD32 | >200 | 1992 | 1562 | 128 |
| WHYKD33 | >200 | 8805 | 637 | 314 |
| WHYKD35 | >200 | 1295 | 518 | 386 |
| WHYKD36 | 67 | 383 | 1044 | 64 |

LC50 (50% lethal concentration) was tested using an XTT assay for cell viability. Measurements listed as 200 represent the upper concentration limit used for testing, whereby the viability is >50% at this upper limit.
EC50 (50% reduction) was based on the concentration whereby the levels were 50% lower than the initial readings based on mKate2 fluorescence (tau tag) or Proteostat levels (fluorescent marker of aggregates).
TI (therapeutic index) was based on the ratio of LC50:EC50, with the upper limit being 200 mM

TABLE 18

PLD1 & PLD2 Activity

| | Proteostat (nM) using pharmacological inhibitor | | | mKate2 (nM) using pharmacological inhibitor | | |
|---|---|---|---|---|---|---|
| Compound | PLD1 | PLD2 | PLD2/PLD1 ratio | PLD1 | PLD2 | PLD2/PLD1 ratio |
| WHYKD36 | 394 | 604 | 1.5 | 1332 | 2284 | 1.7 |

To compare the two isoforms of phospholipase D, samples were treated with either ML298, a PLD2 inhibitor (355 nM) that would yield PLD1 activity or a PLD1 inhibitor (VU0150669, 50 nM) to yield only PLD2 activity.

Example 5

Detection and Results of WHYKD Compounds

A photodiode array (PDA) was used to detect WHYKD8 in mouse brain (FIG. 1). The sample was readily detected with a discrete peak based on time (left) and with a measurable area under the curve (AUC) (inset).

TABLE 16

Biological Testing of WHKD Compounds 1-24

| Compound | % Inhibition Tau/aggregate (1 µM) | % Increase Autophagy Markers | PLD | Cytotoxixity LC50 |
|---|---|---|---|---|
| WHYKD1 | No Effect @ 2 µM | No Effect @ 2 µM | NC | >100 µM |
| WHYKD2 | No Effect @ 2 µM | No Effect @ 2 µM | ND | >100 µM |
| WHYKD3 | No Effect @ 2 µM | No Effect @ 2 µM | NC | >100 µM |
| WHYKD4 | No Effect @ 2 µM | No Effect @ 2 µM | ND | >100 µM |
| WHYKD5 | 35% | 20% | 1.7X | >100 µM |
| WHYKD6 | No Effect @ 2 µM | No Effect @ 2 µM | ND | >100 µM |
| WHYKD7 | No Effect @ 2 µM | No Effect @ 2 µM | ND | >100 µM |
| WHYKD8 | 30% | 25% | 2.8X | >100 µM |
| WHYKD9 | No Effect @ 2 µM | No Effect @ 2 µM | ND | >100 µM |
| WHYKD10 | No Effect @ 2 µM | No Effect @ 2 µM | ND | >100 µM |
| WHYKD11 | No Effect @ 2 µM | No Effect @ 2 µM | ND | >100 µM |
| WHYKD12 | 60% | 40% | 3.4 | >100 µM |
| WHYKD13 | No Effect @ 2 µM | No Effect @ 2 µM | ND | >100 µM |
| WHYKD14 | No Effect @ 2 µM | No Effect @ 2 µM | ND | >100 µM |
| WHYKD15 | 65% | 40% | 3.6 | >100 µM |
| WHYKD16 | No Effect @ 2 µM | No Effect @ 2 µM | ND | >100 µM |
| WHYKD17 | No Effect @ 2 µM | No Effect @ 2 µM | ND | >100 µM |
| WHYKD18 | No Effect @ 2 µM | No Effect @ 2 µM | ND | >100 µM |
| WHYKD19 | 55% | 350 | 3.5 | >100 µM |
| WHYKD20 | No Effect @ 2 µM | No Effect @ 2 µM | ND | >100 µM |
| WHYKD21 | No Effect @ 2 µM | No Effect @ 2 µM | ND | >100 µM |
| WHYKD22 | No Effect @ 2 µM | No Effect @ 2 µM | ND | >100 µM |
| WHYKD23 | No Effect @ 2 µM | No Effect @ 2 µM | ND | >100 µM |
| WHYKD24 | 30% | 15% | ND | >100 µM |

ND—not done,
NC—no change

Figure 2:
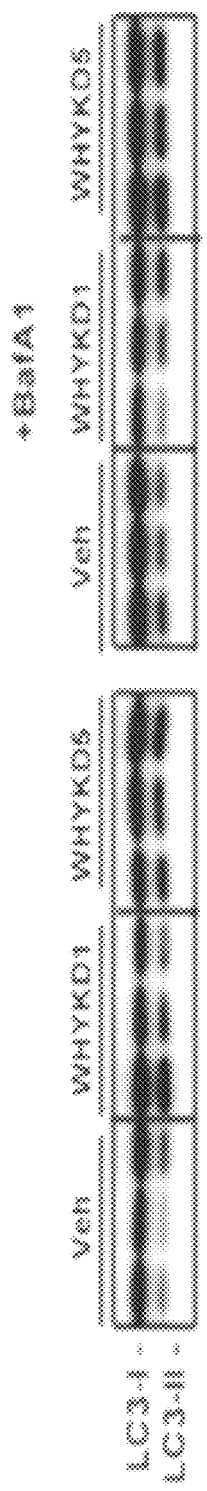
FIG. 2 shows Western blots of LC3-II levels in primary cortical neurons following a 6 hour treatment with WHYKD1 (±BafA1) or WHYKD5.

LC3-II levels were measured in primary cortical neurons following 6 hours of treatment with WHYKD1, WHYKD5, or WHYKD1 BafA1 (FIG. 2). The presence of LC3-II is an indication of autophagy.

Figure 3:
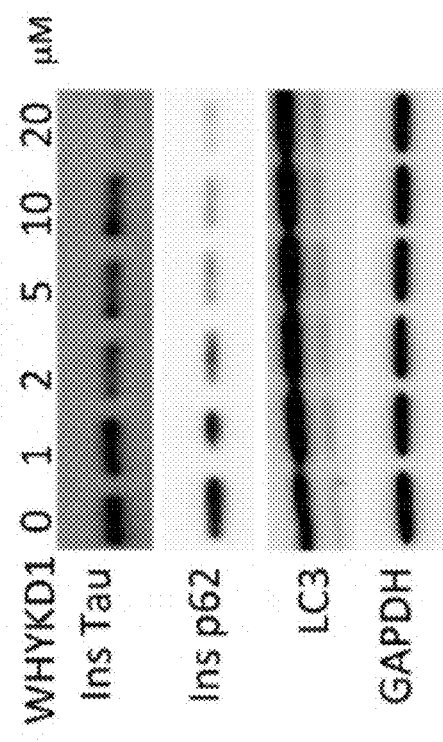
FIG. 3 shows Western blots of LC3-II, tau, and p62 levels in organotypic slice cultures following a 6 hour treatment pith WHYKD1 (top) or WHYKD3, WHYKD5, WHYKD8, WHYKD9, or WHYKD12 (bottom).
Figure 3:
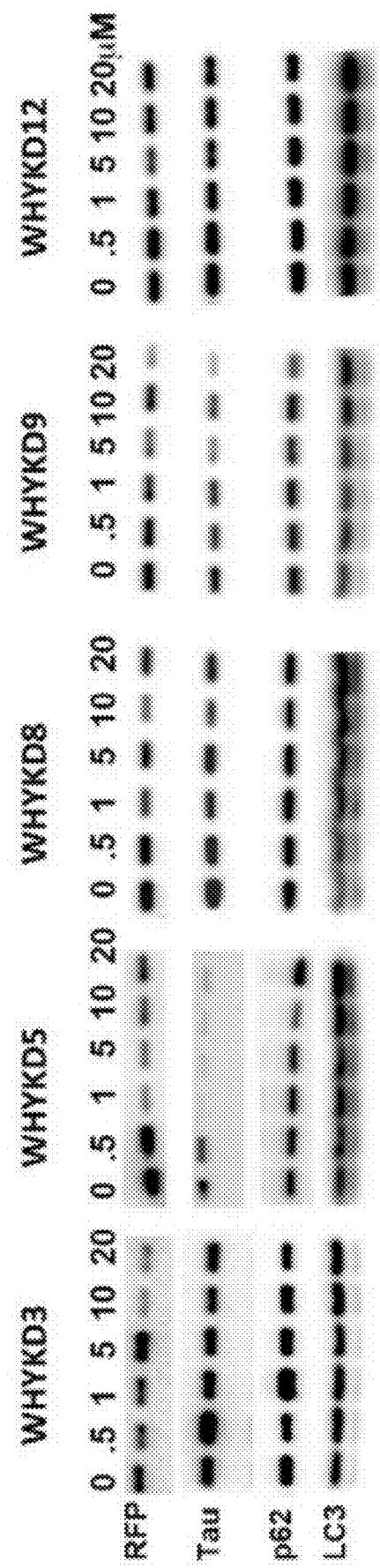

LC3-II levels were then measured in organotypic slice cultures following 6 hours of treatment with WHYKD1 (FIG. 3, top panel). Other compounds in the WHYKD series produced similar results (FIG. 3, bottom panel). RFP is a tag on the tau protein and also can be probed.

These experiments show that the WHYKD series of compounds can induce autophagy and reduce the aggregated forms of tau as well as its aggresome surrogate p62.

Figure 4:
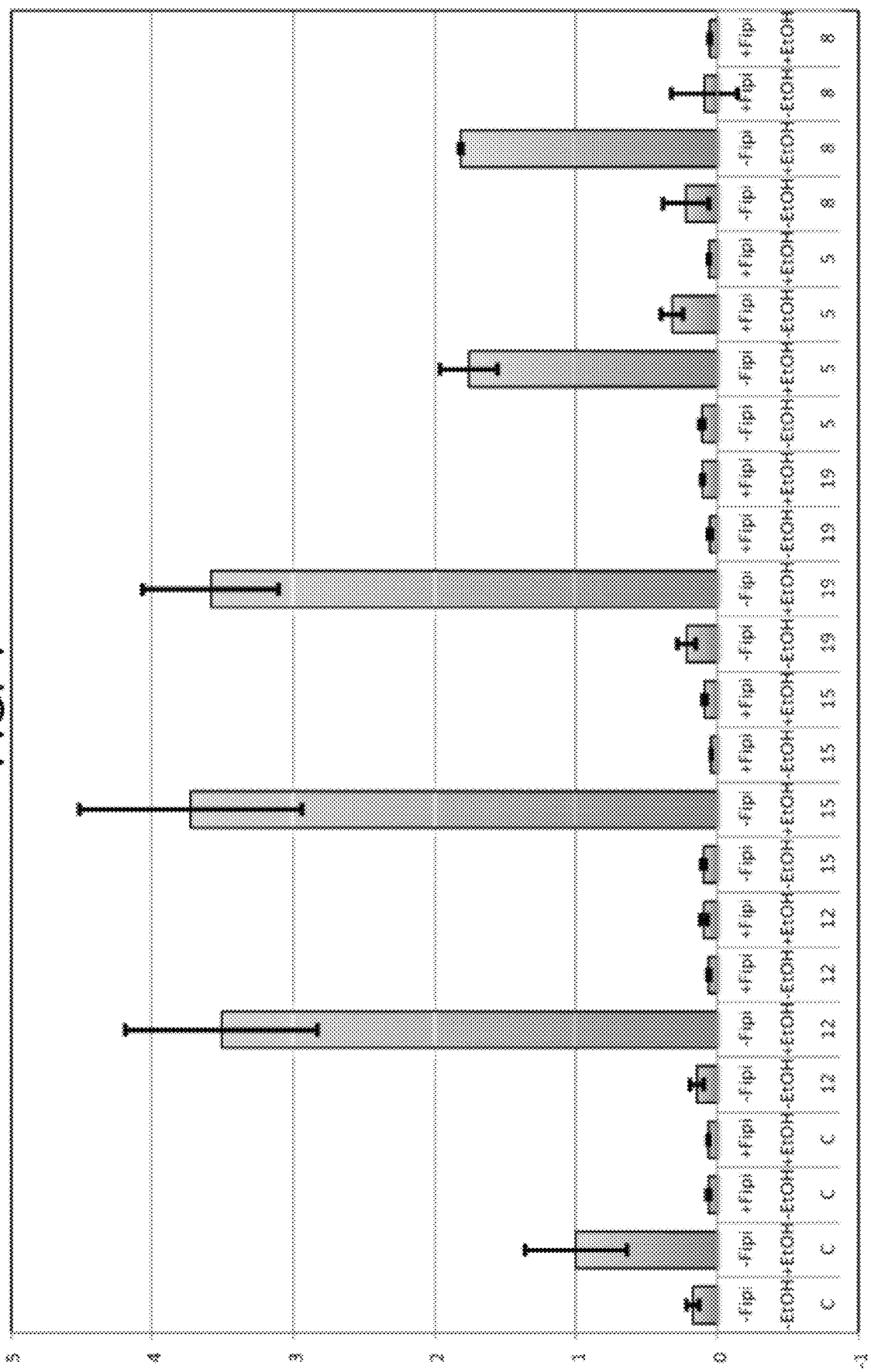
FIG. 4 is a bar graph showing the activation of phospholipase D (PLD) by the WHYKD series compounds (10 µM), and their ability to convert phospholipids to phosphatidylethanols in the presence of ethanol. C=Control, 12=WHYKD12, 15=WHYKD15, 19=WHYKD19, 5=WHYKD5, 8=WHYKD8, Fipi=a noncompetitive inhibitor of PLD activity.
Figure 5:
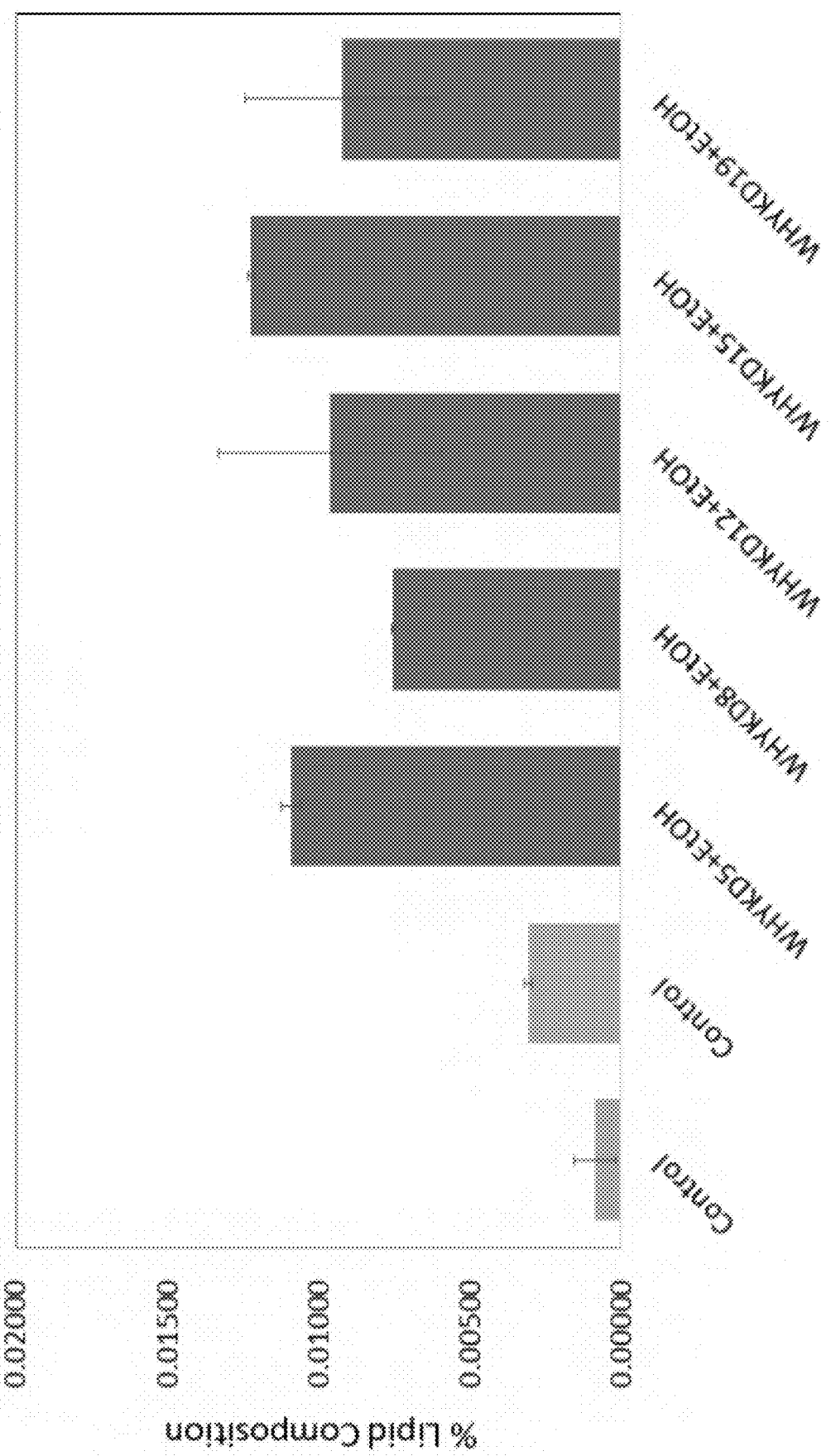
FIG. 5 is a bar graph showing the activation of phospholipase D (PLD) by the WHYKD series compounds (1 µM), and their ability to convert phospholipids to phosphatidylethanols in the presence of ethanol.

PLD activation converts phospholipids to phosphatidylethanols in the presence of ethanol. This conversion was measured to show that the WHYKD series of compounds activate PLD at 100 concentration (FIG. 4) and at 1 μM (FIG. 5). FIPI is a non-competitive inhibitor of PLD activity and was used as a negative control.

All patents, patent applications, and publications cited above are incorporated herein by reference in their entirety as if recited in full herein.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound is selected from the group consisting of:

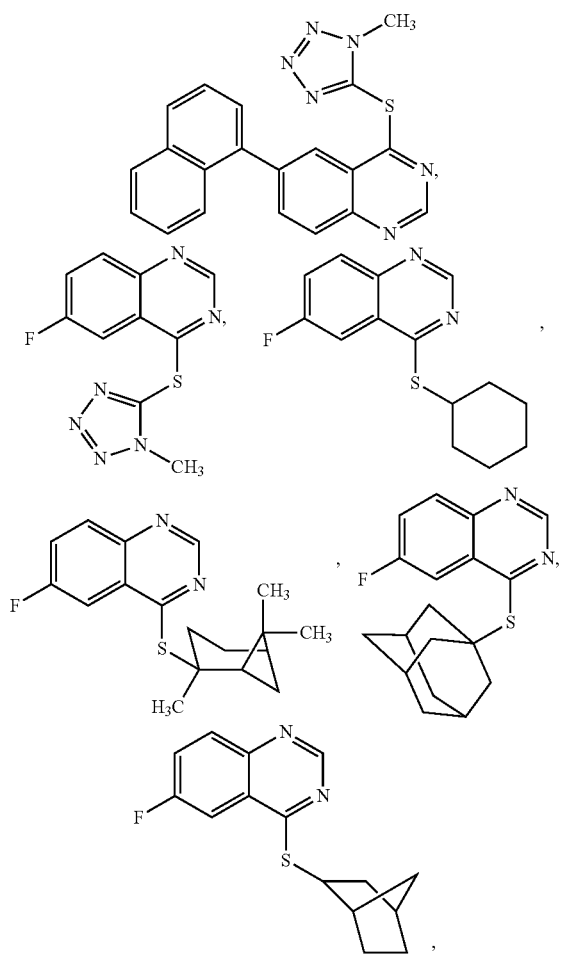

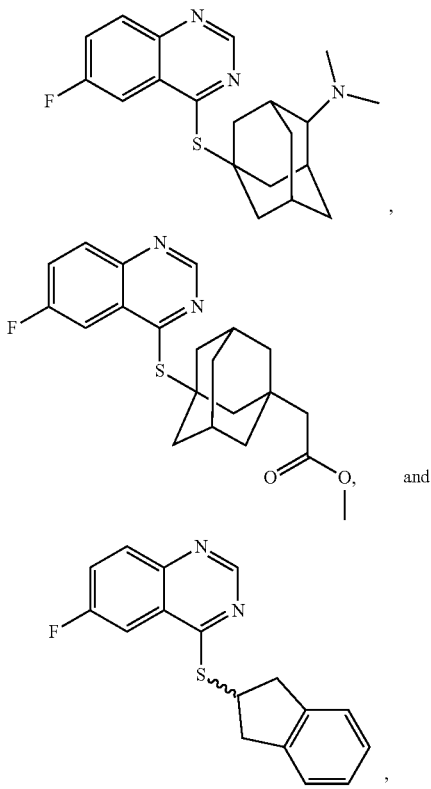

or a salt, enantiomer, racemate, mixture thereof, or combination thereof.

2. The compound of claim 1, wherein the compound is:

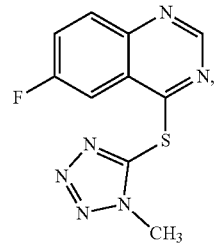 [SMILES: Cn1nnnc1Sc1ncnc2ccc(F)cc12]

or a salt thereof.

3. A compound having the formula (XV):

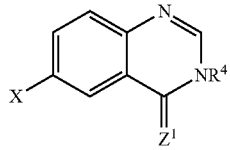

wherein X is halide;

wherein $Z^1$ is O;

wherein $R^4$ is selected from the group consisting of unsubstituted alkyl, Et, $CF_3$, optionally substituted cycloalkyl, optionally substituted heteroaryl, and

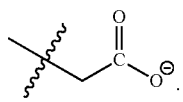 [SMILES: *CC(=O)[O-]]

4. The compound of claim 3, wherein:
X is selected from group consisting of F, Cl, and Br; and
R⁴ is selected from the group consisting of CH₃, Et, CF₃, cycloalkyl, heteroaryl, and

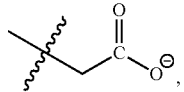 [SMILES: *CC(=O)[O-]]

or a salt, enantiomer, racemate, mixture thereof, or combination thereof.

5. A pharmaceutical composition comprising a compound of claim 1 or claim 3, or a pharmaceutically acceptable salt thereof.

6. A method of treating a neurodegenerative disease comprising administering to a subject in need thereof an effective amount of a compound of claim 1 or claim 3, wherein the neurodegenerative disease is a proteinopathy.

7. The method of claim 6, wherein the proteinopathy is a tauopathy.

8. A method of treating a neurodegenerative disease comprising administering to a subject in need thereof an effective amount of a compound of claim 1 or claim 3, wherein the neurodegenerative disease is Alzheimer's disease.

9. A method of enhancing autophagic flux comprising providing to a cell or a protein aggregate an effective amount of a compound of claim 1 or claim 3.

10. A method of treating a proteinopathy comprising administering to a subject in need thereof an effective amount of a compound of claim 1 or claim 3.

11. A method of treating a tauopathy comprising administering to a subject in need thereof an effective amount of a compound of claim 1 or claim 3.

12. A method of treating a neurodegenerative disease comprising administering to a subject in need thereof an effective amount of the pharmaceutical composition of claim 5, wherein the neurodegenerative disease is a proteinopathy.

13. The method of claim 12, wherein the proteinopathy is tauopathy.

14. A method of treating a neurodegenerative disease comprising administering to a subject in need thereof an effective amount of the pharmaceutical composition of claim 5, wherein the neurodegenerative disease is Alzheimer's disease.

15. A method of enhancing autophagic flux comprising providing to a cell or a protein aggregate an effective amount of the pharmaceutical composition of claim 5.

16. A method of treating a proteinopathy comprising administering to a subject in need thereof an effective amount of the pharmaceutical composition of claim 5.

17. A method of treating a tauopathy comprising administering to a subject in need thereof an effective amount of the pharmaceutical composition of claim 5.

18. A method of treating a neurodegenerative disease comprising administering to a subject in need thereof an effective amount of a compound having the following formula:

wherein X is H or halide;
wherein Z¹ is O;
wherein R⁴ is selected from the group consisting of H, optionally substituted alkyl, Et, CF₃, optionally substituted cycloalkyl, optionally substituted aryl, optionally substituted heteroaryl, and

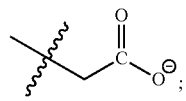 [SMILES: *CC(=O)[O-]]

and
wherein the neurodegenerative disease is a proteinopathy.

19. The method of claim 18, wherein the proteinopathy is a tauopathy.

20. The method of claim 18, wherein the proteinopathy is Alzheimer's disease.

21. A method of treating a neurodegenerative disease comprising administering to a subject in need thereof an effective amount of a compound of formula (II):

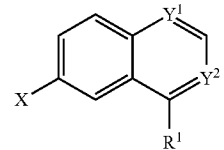

wherein Y¹ and Y² are N;
wherein X is selected from the group consisting of H, halide, and aryl;
wherein R¹ is selected from the group consisting of optionally substituted thioheteroaryl, and optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof,
wherein the neurodegenerative disease is Alzheimer's disease.

22. A method of treating a neurodegenerative disease comprising administering to a subject in need thereof an effective amount of a compound of formula (II):

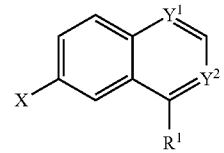

wherein Y¹ and Y² are N;
wherein X is selected from the group consisting of H, halide, and aryl;

wherein $R^1$ is selected from the group consisting of optionally substituted thioheteroaryl, and optionally substituted thiocycloalkyl wherein 1-3 carbon atoms of the cycloalkyl is optionally replaced with a heteroatom selected from the group consisting of O, S and N, and thioaryl, or a salt, enantiomer, racemate, mixture thereof, or combination thereof, wherein the neurodegenerative disease is a proteinopathy.

23. The method of claim 22, wherein the proteinopathy is a tauopathy.

* * * * *